US006174890B1

(12) United States Patent
Riga et al.

(10) Patent No.: US 6,174,890 B1
(45) Date of Patent: Jan. 16, 2001

(54) ANTI-STRESS, ANTI-IMPAIRMENT AND ANTI-AGING DRUG AND PROCESS FOR MANUFACTURING THEREOF

(76) Inventors: Dan Riga; Sorin Riga, both of Sector 1, Belgrade Street 7, Bucharest (RO), R-71248

( * ) Notice: Under 35 U.S.C. 154(b), the term of this patent shall be extended for 0 days.

(21) Appl. No.: 08/750,159

(22) PCT Filed: Jun. 2, 1994

(86) PCT No.: PCT/RO94/00003

§ 371 Date: Feb. 28, 1997

§ 102(e) Date: Feb. 28, 1997

(87) PCT Pub. No.: WO95/33486

PCT Pub. Date: Dec. 14, 1995

(51) Int. Cl.[7] .................................................. A61K 645/06
(52) U.S. Cl. .......................... 514/270; 514/276; 514/904; 514/905
(58) Field of Search .................................. 514/276, 270, 514/904, 905

(56) References Cited

U.S. PATENT DOCUMENTS 3,493,659   2/1970   Magid .

OTHER PUBLICATIONS

Stress and Psychiatry, Wilder, et al.; pp. 1198–1203; Comprehensive Textbook of Psychiatry/IV, vol. 1; Williams and Wilkins, Baltimore, 1985.
Neurobiology of Aging; Terry et al.; Aging, vol. 3; Raven Press, New York, 1976.
Subcellular genesis of the nerve lipofuscin pigments; Riga, etal.;Acta Anatomica, vol. 99, No. 3, 1977.
Executive stress goes global; Cooper, et al.; International Management, vol. 39, No. 5, pp. 42–48; May 1984.
Benzodiazepines—The Opium of the Masses?; M. Lader; pp. 609–615;Commentaries in the Neurosciences, Pergamon Press, Oxford, 1980.
Prevention of Mental, Psychosocial and Neurological Disorders in the European Region; W.H.O. Europe, 38th Session, Copenhagen, Sep. 1988.
The Effects of Caffeine; I.B. Syed; Journal of the American Pharmaceutical Association, vol. NS 16, pp. 568–572, Oct. 1976.
Handbook of Psychopharmacology; Iversen, et al.; vol. 11 Stimulants; Plenum Press, New York, 1978.
Changes in Lipofuscin pigments of rat . . . ; Riga, et al.; 9th Internation Congress of Gerontology, vol. 3, abstract No. 1103, p. 383, Kiev, USSR 1972.
Age–Associated Changes in the Hypothalamus of the Guinea Pig: Effect of Dimethylaminoethyl p–chlorophenoxyacetate. An Electron Microscope and Histochemical Study; M. Hasan, et al.; Exp. Geront., vol. 9, p. 153–159, 1974.
Effects of Centrophenoxine of the Lipofuscin Pigments in the Nervous System of Old Rats; Riga, et al.; Brain Research, 72(1974), p. 265–275.
Dynamics of lipofuscin pigments—directing factor of brain aging; Riga, et al.; p. 70; VIè Congres Medical International, Prague, 1976.
An Attempt to Answer the Questions of Theoretical Gerontology on the Basis of the Membrane Hypothesis of Aging; Nagy; Advances in the Biosciences, vol. 64; 1987, p. 393–413.
Selected Histochemical and Histopathological Methods; Thompson, et al.; p. 1201–1234, 1305–1326; 1966.
Methodology of lipofuscin pigment research in neuroanatomy; Riga, et al.; Israel Journal of Medical Sciences, vol. 14, No. 8, p. 903, 1978.
Intracellular Localization of Lipofuscin Age Pigments in the Nervous System; Samorajski, et al.; Journal of Gerontology, vol. 19, p. 262–276, Jul., 1964.
Fine Structural Changes in the Lateral Vestibular Nucleus of Aging Rats; Johnson, et al.; Mechanics of Aging and Development, vol. 3, p. 203–224, 1974.
Clinical, Morphologic, and Neurochemical Aspects in the Aging Central Nervous System; Brody, et al.; Aging, vol. 1, New York, 1975.
The Deposition of Aging Pigment in the Human Cerebral Cortex; Brody; Journal of Gerontology, vol. 15, Jul. 1960, p. 258–261.
Macromolecular synthesis in developing and aging brain; Condorelli, et al.; Macromolecules in the Functioning Cell; p. 243–257, 1988.
Antagonic–Stress, Anew Treatment in Gerontopsychiatry and for a Healthy Productive Life; Predescu, et al.; p. 315–331; Pharmacology of Aging Processes, vol. 717, 1994.

*Primary Examiner*—Keith D. MacMillan
(74) *Attorney, Agent, or Firm*—Cohen, Pontani, Lieberman & Pavane

(57) ABSTRACT

The invention relates to a new pharmacotherapeutical strategy, to an anti-stress, anti-impairment and anti-aging drug and to a process for its manufacturing. The drug has an etio-pathogenic and homeostatic action, was preclinically tested and clinically checked up in geriatric, neurologic, psychiatric and stress-dependent pathology. The drug achieves a synergistic biological, neurometabolic and celltrophic composition, being elaborated by the association of the following active principles: a) against oxidative and catabolic stress; methionine with aminoethanol phenoxyacetates and/or aminoethyl phenoxyacetamides; b) against anabolic stress; hydroxopyrimidine carboxylates and/or oxopyrrolidine acetamides with potassium, zinc and lithium; c) vasodilative and normolipidemic; nicotinic, alcohol and/or acid, or its derivatives, with magnesium and iodine; d) energo-active and e) anti-toxic; aspartate; fructose; vitamin $B_1$; vitamin $B_6$; monoacid phosphate and sulfate. The process for manufacturing the drug stipulates; a) pharmaceutical preparation in two complementary types of capsules or coated tablets, gastrosoluble and enterosoluble, the last being enteric coated; b) prolonged-release of vasodilator from the enterosoluble unit.

9 Claims, 9 Drawing Sheets

Figure 1:
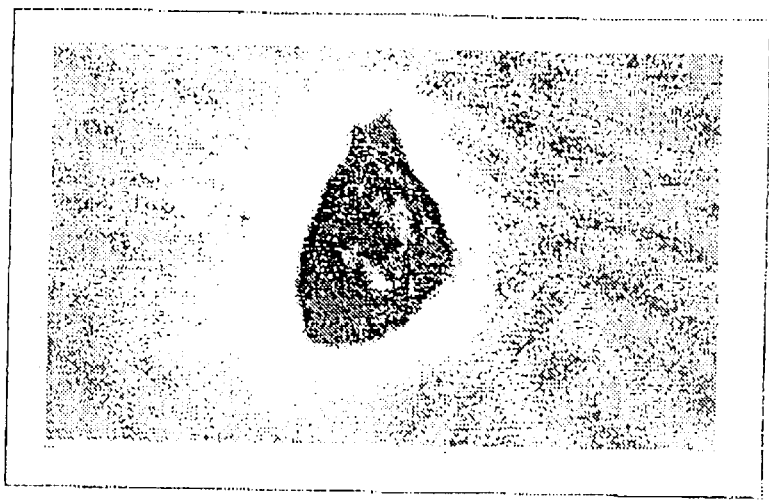
Figure 2:
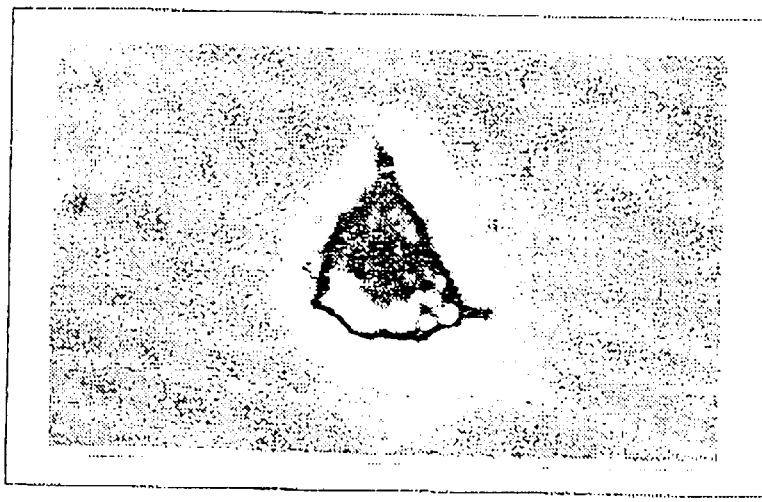
Figure 3:
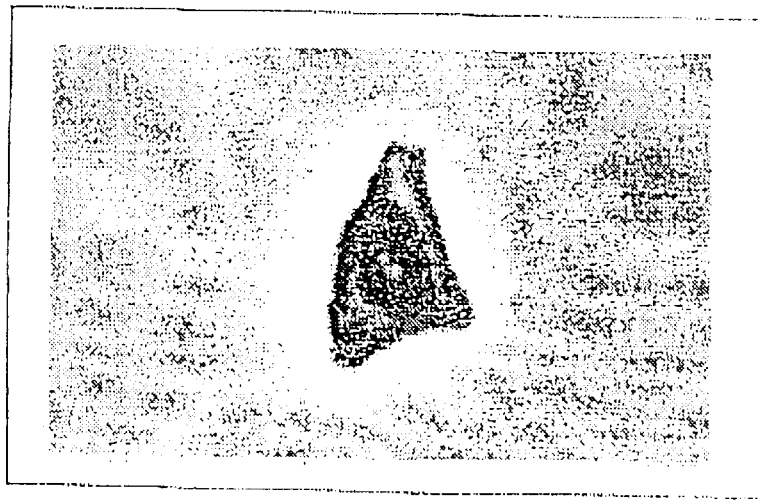
Figure 4:
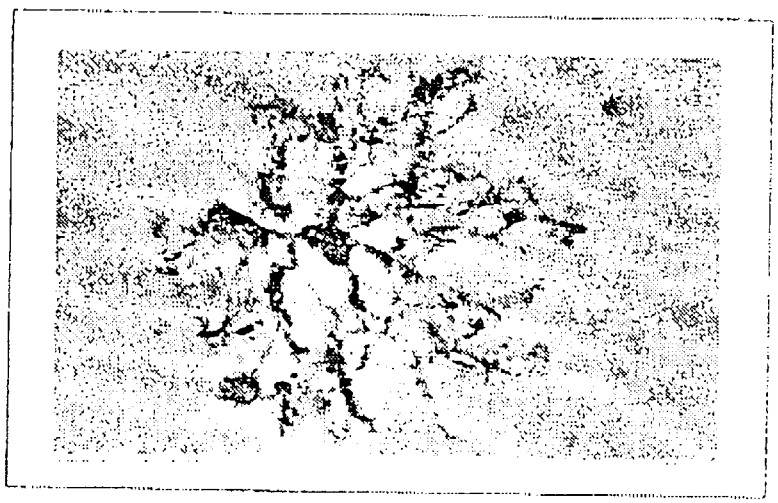
Figure 5:
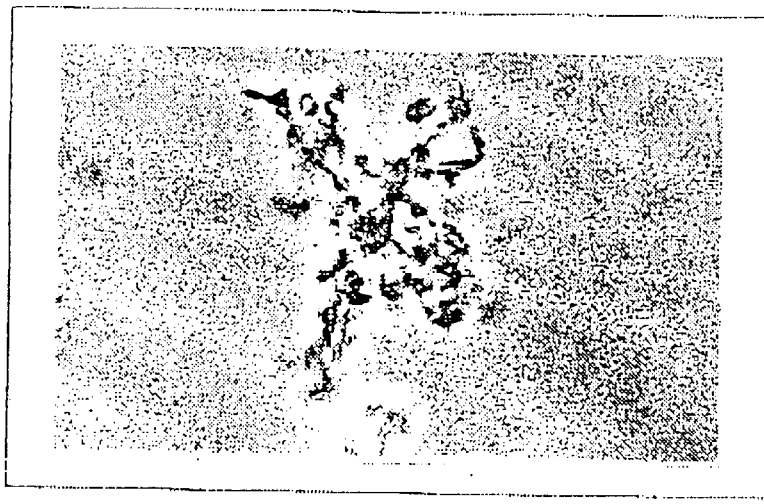
Figure 6:
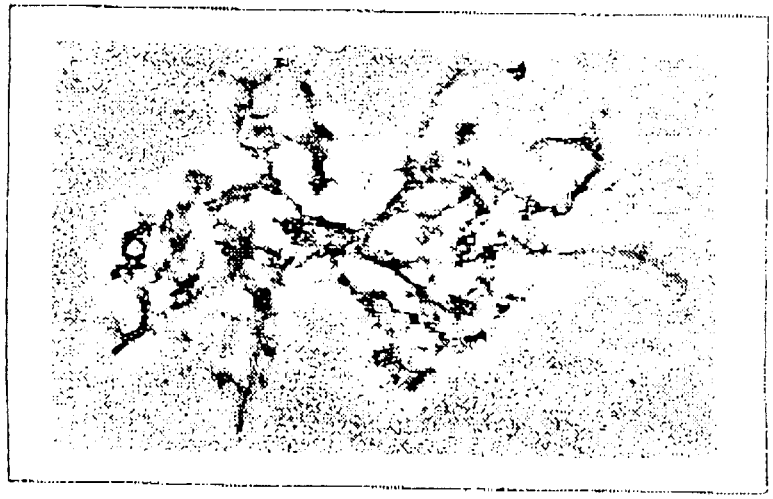
Figure 7:
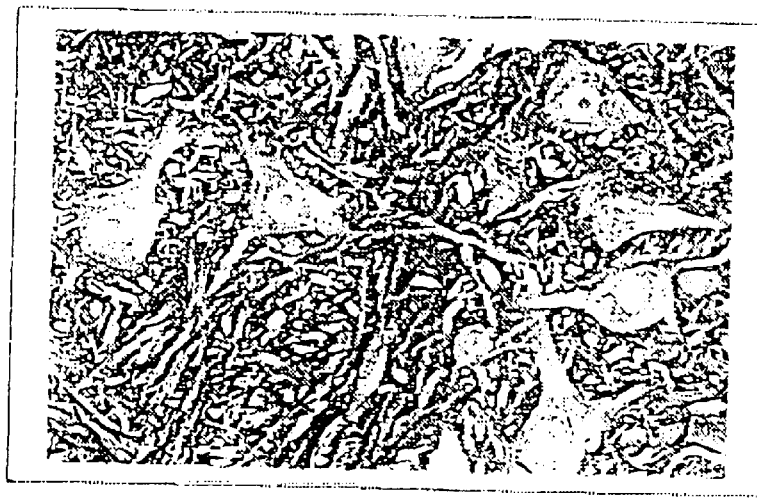
Figure 8:
Figure 9:
Figure 10:
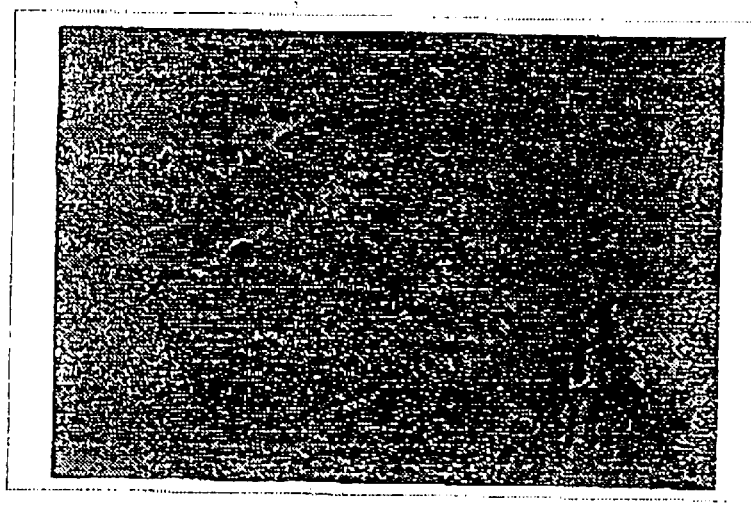
Figure 11:
Figure 12:
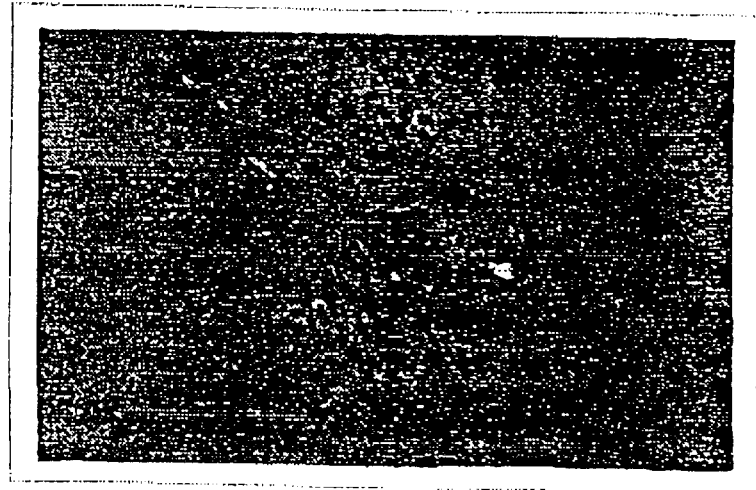
Figure 13:
Figure 14:
Figure 15:
Figure 16:
Figure 17:
Figure 18:
Figure 19:
Figure 20:
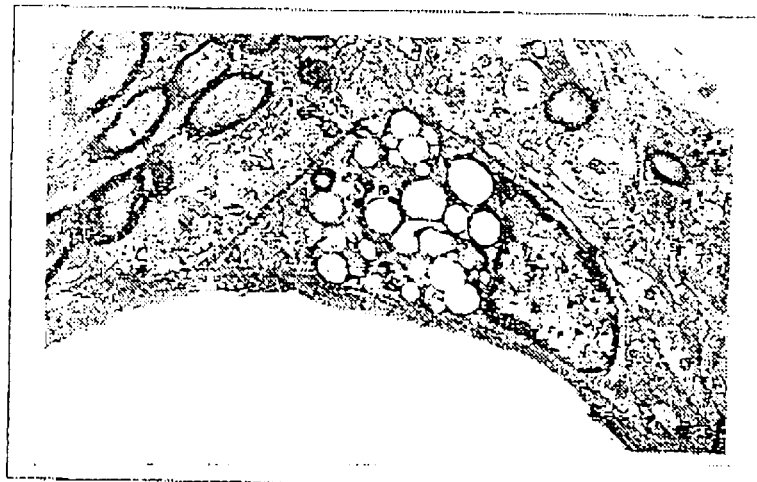
Figure 21:
Figure 22:
Figure 23:
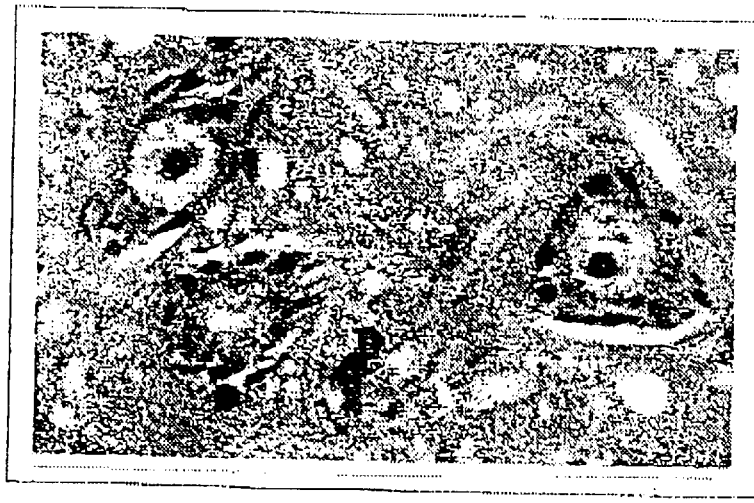
Figure 24:
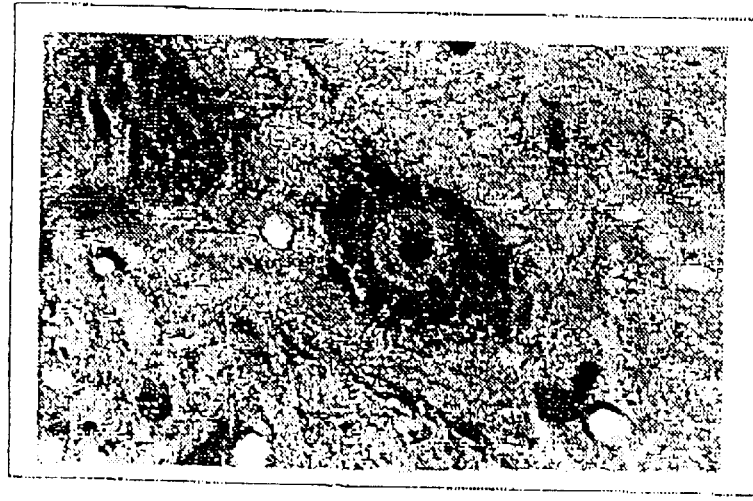
Figure 25:
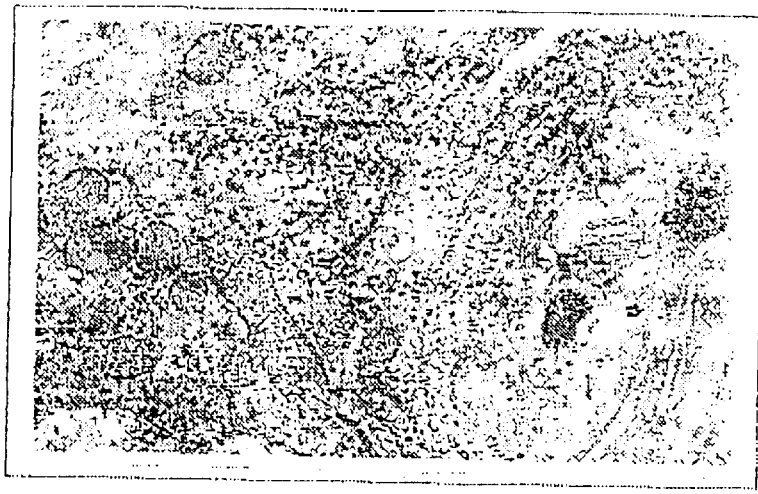
Figure 26:
Figure 27:
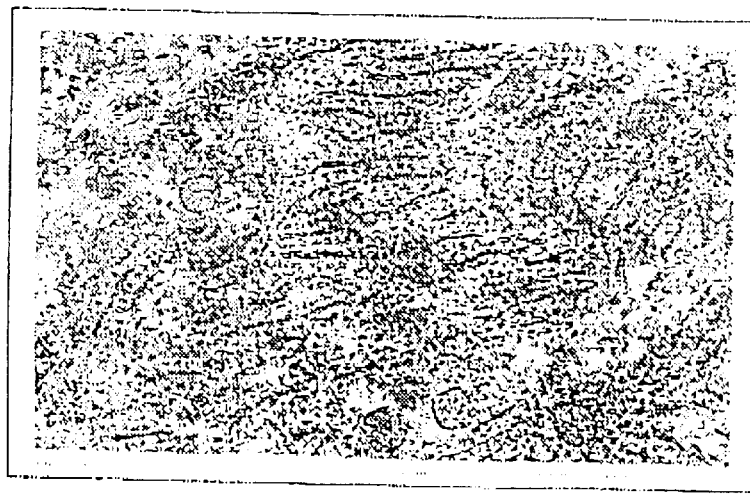

ANTI-STRESS, ANTI-IMPAIRMENT AND ANTI-AGING DRUG AND PROCESS FOR MANUFACTURING THEREOF

TECHNICAL FIELD

The present invention relates to an orally-administered drug having anti-stress, anti-impairment and anti-aging etio-pathogenic actions, and manifold therapeutic efficiency, as a result of its synergistic biological, neurometabolic and cell-trophic composition. The invention also relates to a process for its manufacturing. This drug supports and enhances the adaptation capability and the neuropsychic and biological resistance, simultaneously achieves the anti-stress protection of the brain, liver and heart, and corrects the main ultrastructural and metabolic imbalances brought about by acute and chronic stress, prolonged biological wear and tear, oxidative stress, ischemia-hypoxia, chronic alcoholism and premature aging, thus being meant for stress-dependent pathology. The non-conventional pharmaceutical process for its manufacturing further provides the controlled guidance in the release and absorption of the active substances, and the prolonged cerebral vasodilative action, which together promote maximum bioavailability and therapeutic efficacy.

BACKGROUND ART

Acute and chronic stress, a negative and permanent characteristic of present-day life, comprises the unfolding of three processes: first—the aggression of the body by stressors, in a continuous growth, diversification and perpetuation; second—the body response, which may be adaptively, maladaptively or pathologically stress-dependent; and third—the intense, accelerated and chronically accumulated wear and tear of the brain and of the organism, premature aging.

The adaptive response of the body (the general adaptation syndrome) consists of three successive stages: immediate adaptation, long-term adaptation and the stage of exhaustion—neuropsychic and biological impairment (SELYE, H., The evolution of the stress concept, American Scientist, 61, 692–699, 1973). Chronic wear and tear means the neuropsychic and biological progressive incapacitation; it results in the decrease of the adaptation capability and in the diminution of body vitality and resistance, and it is the consequence of accumulation in the course of time and stressful life events and stress-induced lesions. When the adaptation capabilities of the organism are exceeded, due to the intensification, frequency and chronicization of stress and impairment, diseases of adaptation appear, meaning the stress-dependent pathology: neuropsychiatric and psychosomatic illnesses (WILDER, J. F., PLUTCHIK, R., Stress and psychiatry (Cap. 25.11), pp. 1198–1203, In: KAPLAN, H. I., SADOCK, B. J. (Eds.), Comprehensive Textbook of Psychiatry/IV, vol. 1, Williams and Wilkins, Baltimore, 1985).

The human brain, through its triple functionality—neurobiological, psychic and social—and due to the loss, after birth, of the neuron regeneration capacity through cell division, represents the global "receiver" of stresses (ischemic, hypoxic, oxidative etc.) and the "storage" of chromic, progressive, neuropsychic and biological impairment. Thus, in the central nervous system, specific ultrastructural and biochemical imbalances and lesions are accumulated, reaching all levels of metabolism (energy, anabolism, catabolism), then they extend with age and determine the incapacitation of the brain and body functions. The cerebral blood flow diminution as a consequence of stress and aging (progressive chromic hypoxia) and the neuronal hypoanabolism (the disturbance and decrease of nucleic acid and protein synthesis, the reduction and impairment of Nissl bodies—crowds of rough endoplasmic reticulum and free ribosomes—and of Golgi apparatus) induce the diminution of plasticity and anabolic regeneration, both functional (enzymes and neurotransmitters) and ultrastructural (neurosomes and extensions), (TERRY, R. D., GERSHON, S. (Eds.), Aging, vol. 3 (Neurobiology of Aging), Raven Press, New York, 1976). Oxidative stress, neuronal hypercatabolism, lipid peroxidation, especially of membranes, and the premature chronic impairment of subcellular organelles, mainly mitochondria, in all cases finally result in a progressive accumulation of lipofuscin pigments (wear and tear pigments, age pigments, tertiary lysosomes, insoluble subcellular wastes coming from peroxidation, polymerization and cross-linkages by free radicals) in neurons and glial cells (RIGA, D., RIGA, S., POPESCU, A., CONSTANTINESCU, E., PERIETEANU, M., Subcellular genesis of the nerve lipofuscin pigments, 4th European Anatomical Congress, Basle, Switzerland, 1977; Acta Anatomica, 99, 307–308, 1977; ZS.-NAGY, I. (Ed.), Lipofuscin—1987: State of the Art, Academiai Kiado, Budapest, 1988).

The necessity to develop a specific drug having an etio-pathogenic action against stress, impairment and premature aging was determined by the profound negative consequences of stress:
 a) at the individual level—professional failure, disease, premature aging and death, and
 b) at the level of the whole society—important economic and social losses, direct and indirect (COOPER, C., ARBOSE, J., Executive stress goes global, International Management, 39, 42–48, 1984).

From the prior art it can be seen that efforts made for the production of drugs efficient in the control and treatment of stress and impairment have so far failed to produce a specific drug with an etio-pathogenic action; only symptomatological purposes or energizing effects have been fulfilled.

Thus, for improving the symptomatology induced by stress, dysadaptation, maladaptation responses to stress and the stress-related disorders (anxiety, depression, asthenia, sleeplessness, neurotic, neurovegetative and psychosomatic disorders) the use of psychotropic medication is known (POLDINGER, W., SCHMIDLIN, P. E., WIDER, F., Index Psychopharmacorum, H. Huber, Bern, 1983). Depending on the prevailing symptomatology, the following are known as having been used:
 a) anxiolytics (minor tranquilizers): diazepam, meprobamate, methylpentynol, etifoxine;
 b) neuroleptics (major tranquilizers): chloropromazine, promethazine, azaperone;
 c) beta-adrenergic blockers: bunitrolol;
 d) antidepressants: tricyclic, tetracyclic compounds, alone or associated with neuroleptics;
 e) psychostimulants: caffeine, amphetamine or derivatives;
 f) sedatives and hypnotics: combining in the formula phenobarbital and codeine (Romanian Patents nos. 60376 and 64161).

These psychotropic drugs have the disadvantage of representing only a predominant symptomatic medication, without an etio-pathogenic action against stress; they do not reduce chronic impairment caused by stress, they do not act against stress through anabolic regeneration, they modify the normal (anti-stress) reactions of body adaptation and bring about numerous adverse reactions. Furthermore, the anxiolytic and psychostimulant drugs (of the amphetamine and caffeine type) often call for increasing posology, due to phenomena of acquired tolerance and determine, as important adverse reactions, the dependence on psychoactive substances (LADER, M., Benzodiazepines—the opium of the masses?, pp. 609–615, In: SMITH, A. D., LLINAS, R., KOSTYUK, P. G. (Eds.), Commentaries in the Neurosciences, Pergamon Press, Oxford, 1980; W.H.O. Europe, Prevention of Mental Psychosocial and Neurological Disorders in the European Region, 38th Session, Copenhagen, 12–17 September, 1988).

One also knows many anti-stress drug compositions used for energizing, activatory, stimulating, trophic, tonic, fortifying—neuropsychic and/or biological—purposes. They are employed in treating disorders caused by acute and chronic stress, by stress-dependent pathology and especially against their most frequent consequences: nervous, psychic and biological exhaustion, accelerated chronic impairment, premature senescence.

a) Some of these compositions contain polyvitamins: hydrosoluble (American Medical Association, AMA Drug Evaluations, Publishing Sciences Group, Acton, Mass., 1973), hydrosoluble together with liposoluble (U.S. Pat. No. 3,493,659), or polyvitamins with bioelements (French Patent no. 7404 M);

b) Other mixtures associate amino acids with or without vitamins (acetylaspartic acid, arginine glutamate, citrulline with folic acid), or are based on aspartates (Romanian Patents nos. 55069 and 77472; French Patent no. 2521429), on glutamates (Romanian Patent no. 76141), or cysteine (Romanian Patent no. 74505), arginine (French Patent no. 2494113), or complex combinations usually built up, alongside with the above mentioned amino acids, from glycine, lysine, tyrosine, ornithine, histidine (French Patent no. 5937 M; Romanian Patent no. 76044);

c) Other associations comprise stimulating substances and combinations thereof: amphetamine, amphetamine with caffeine, or caffeine with vitamins (Romanian Patents nos. 62137 and 66014).

These products, even when they are complex drug associations, have the drawback of not achieving an etio-pathogenic anti-stress therapy by simultaneous coupling of some multiple (vasodilative, normolipidemic, energo-active, anti-toxic, of catabolic regulation—lipofuscinolysis and anabolic regeneration) actions; they are not preclinically tested in antagonization of the experimental stress induced in animals, they cannot prevent or decelerate nervous wear and tear by antagonization of the oxidative stress and do not support the natural adaptation mechanisms—anti-stress mechanisms. Furthermore, especially drugs that associate methylxanthines and/or amphetamines are disadvantageous, because they form an incomplete, limited medication, of short-term effects, which in case of chronic administration, or in large doses, determine other new imbalances, contributing to the enhancement of those pre-existent, to the diminution of neuropsychic and biological resistance to stress, intensifying cellular catabolism and maladaptive reactions against stress; moreover, their use induces many adverse reactions (SYED, I. B., The effects of caffeine, Journal of the American Pharmaceutical Association, NS 16, 568–572, 1976; IVERSEN, L. L., IVERSEN, S. D., SNYDER, S. H. (Eds.), Handbook of Psychopharmacology, vol. 11 (Stimulants), Plenum Press, New York, 1978).

The use of methionine in hepatic pathology, as a hepatoprotective compound is well known (WADE, A., REYNOLDS, J. E. F. (Eds.), The Extra Pharmacopoeia, The Pharmaceutical Press, London, 1978). We found out by successive investigations that methionine additionally has a specific neurotropic action and interferes etio-pathogenically against stress. In this way we demonstrated the antagonization effect of chronic oxidative stress, determined by the diminution of lipofuscin pigments in the brain (telencephalon and diencephalon) of old rats, using quantitative histochemical methods (RIGA, S., PAMBUCCIAN, G., OERIU, S., Changes in lipofuscin pigments of rat central nervous system under —SH groups' releasing substances' influence, 9th International Congress of Gerontology, vol. 3 (Section Session, Abstracts), abstract no. 1103, p. 383, Kiev, U.S.S.R., 1972). Subsequently, we emphasized its complex action anti-stress, anti-impairment and anti-aging (catabolic regulation—anti-lipofuscinogenesis, lipofuscinolysis, and anabolic regeneration—the increase of RNA synthesis) at the nervous system level of old rats, using a complex methodology: selective isolations of living nerve cells from brain, morphometrical and biochemical methods (RIGA, S., Studies on Nucleic Acids in the Central Nervous System in Senescence Processes, Ph. D. Thesis, Institute of Medicine and Pharmacy, Bucharest, 1976, in Romanian).

It is also known that meclofenoxate, thanks to its actions of energetic and metabolic regulation on nerve cells, has a wide-spread area of clinical use in psychiatry, neurology as well as in the pathology determined by the hypoxic stress aggression of the brain—geriatrics, neurosurgery, anesthesiology, intensive care (COIRAULT, R., DELIGNE, P., ROUIF, J., Une orientation therapeutique nouvelle. L'A.N.P. 235 (ester dimethyl-amino-ethylique de l'acide para-chloro-phenoxy-acetique), Agressologie, 1, 113–138, 1960, in French). Afterwards, using light microscopy-histochemistry (qualitative only), the property of meclofenoxate to decrease lipofuscin pigments in the nervous system of old guinea pigs was emphasized (NANDY, K., BOURNE, G. H., Effect of centrophenoxine on the lipofuscin pigments in the neurons of senile guinea-pigs, Nature (Lond.), 210, 313–314, 1966); it was also demonstrated by electron microscopy (HASAN, M., GLEES, P., EL-GHAZZAWI, E., Age-associated changes in the hypothalamus of the guinea pig: effect of dimethylaminoethyl p-chlorophenoxyacetate. An electron microscopic and histochemical study, Experimental Gerontology, 9, 153–159, 1974). Our researches, having priority as preclinical methodology (quantitative—morphometry and qualitative—type of distribution, autofluorescence, histochemistry) and our trivalent experimental pattern (statistical comparison of three groups—control young, control old and treated old) have demonstrated the meclofenoxate action of specific and intense decrease of lipofuscin pigments in the brain of old rats; based on that, the authors of the present invention introduced in the scientific literature in the art the concept of lipofuscinolysis (RIGA, S., RIGA, D., Effects of centrophenoxine on the lipofuscin pigments in the nervous system of old rats, Brain Research, 72, 265–275, 1974), sustaining it also by electron microscopy (RIGA, D., RIGA, S., Selektive lipofuszinolytische Effekte von Centrophenoxin am Nervensystem alter Ratten, pp. 22–27, In: KUGLER, J. (Ed.), Himstoffwechsel und Himdurchblutung, Schnetztor Verlag, Konstanz, Schweiz, 1977). Later on this concept was used by other authors too. As a result of its lipofuscinolytic action, proof of the antagonization of oxidative stress, meclofenoxate acts etio-pathogenically against brain stress, impairment and aging (RIGA, S., RIGA, D., Dynamics of lipofuscin pigments, directing factor of brain aging, 6e Congres Medical International de la Federation Internationale des Resistants, (F.I.R.), Prague, Tchecoslovaquie, le 30 novembre—3 decembre 1976, Resumes, p. 70, 1976) and in deceleration of aging rate (ZS.-NAGY, I., An attempt to answer the questions of theoretical gerontology on the basis of the membrane hypothesis of aging, Advances in the Biosciences, 64, 393–413, 1987).

The two above mentioned substances, administered separately or without an anti-stress potentiation by means of a neurometabolic composition with an etio-pathogenic action, are disadvantageous because they offer only an incomplete protection of the brain against stress, impairment and aging, while their actions of functional and metabolic regulation, as well as of subcellular regeneration are only partial.

DISCLOSURE OF INVENTION

The drug with anti-stress, anti-impairment and anti-aging etio-pathogenic action, according to the invention, carries out a synergistic biological, neurometabolic and cell-trophic composition, elaborated in a specific anti-stress therapeutic conception, by association and synergism of the following active principles:

- a) anti-oxidative and anti-catabolic stress compounds (anti-lipofuscinogenesis, lipofuscinolytics and for lipofuscin elimination): methionine plus aminoethanol phenoxyacetates and/or aminoethyl phenoxyacetamides);
- b) anti-anabolic stress components (for functional and ultrastructural anabolic regeneration): hydrooxopyrimidine carboxylates and/or oxopyrrolidine acetamides with potassium, zinc and lithium;
- c) vasodilators (anti-hypoxic and anti-ischemic stress) and normolipidemic compounds: nicotinic alcohol and/or acid or derivatives thereof with magnesium and iodine;
- d) energo-active and e) anti-toxic components: aspartate, fructose, vitamin $B_1$, vitamin $B_6$, monoacid phosphate and sulfate.

The process for drug manufacturing, according to the present invention, in order to fulfill in oral administration a maximum bioavailability and therapeutic efficiency, stipulates:

- a) for controlled delivery in the release and absorption of the active compounds from the drug, the pharmaceutical preparation of the composition in two complementary types of capsules or film-coated tablets (gastrosoluble and enterosoluble units), the latter being enteric-coated, and
- b) for achieving the prolonged anti-ischemic and anti-hypoxic actions, the nicotinic alcohol or acid, or its derivatives from the composition of the enterosoluble capsule or film-coated tablet is retarded, under the form of granule or tablet.

The drug, according to the invention, offers the following advantages:

- it represents a new drug and a new pharmacotherapeutical strategy in the fields of health promotion and in the prophylaxis, control and treatment of stress, biological wear and tear, premature aging, stress-related illnesses;
- it was elaborated and tested according to the biological drug conception, carrying out a synergistic biological, neurometabolic and cell-trophic (cerebral, hepatic, myocardial and general) composition, resulting in a multiple therapeutic efficacy, without toxicity and adverse reactions, without tolerance and dependence;
- it was created and checked up in a specific therapeutic conception, namely etio-pathogenic and homeostatic, against stress, impairment and aging, thus ensuring higher therapeutic efficiency, based on its active constituents (anti-oxidative and anti-catabolic stress, anti-anabolic stress, vasodilative—anti-hypoxic and anti-ischemic stress—and normolipidemic, energo-active and anti-toxic compounds), in free radical pathology, hypercatabolic and hypoanabolic states, in hypoxic-ischemic pathology, in dyslipidemias, in energetic exhaustion and toxic-deficient pathology;
- its biological composition and its specific anti-stress action determine a larege area of prophylactic, therapeutic and recovering uses, for the whole scale of ages (child, young man, adult, old man), for both healthy and sick persons;
- it is meant for healthy people, especially during activities with a high stressant and performing coefficient, because it antagonizes the anti-homeostatic action of stress and impairment (at neuropsychic and biological levels) and enhances the working power in overstressing conditions through increasing the resistance to psychic (intellectual) and physical (biological) effort;
- it is meant for patients in stress-dependent, psychosomatic, psychiatric and neurologic pathology, in geriatrics and internal medicine.

The administration of the drug, according to the present invention, may efficiently contribute to the maintainance and improvement of the mental and biological state of health, to a significant reduction of economic and social losses, determined in the whole of society by stress, biological impairment, premature aging and by the stress-dependent pathology.

The pharmaceutical procedure for manufacturing the drug, according to the present invention, offers the following advantages:

- in case of oral administration, it allows maximum bioavailability and therapeutic efficiency;
- it ensures controlled guidance in the release and absorption of active substances from the drug, by formulating the composition in two complementary types of pharmaceutical units (capsules or film-coated tablets): gastrosoluble and enterosoluble;
- for the enteric coating of the enterosoluble unit, it employs a technologic procedure completely non-toxic and non-polluting, namely the spraying with aqueous dispersion of gastroresistant-enterosoluble polymer;
- it ensures a prolonged or sustained anti-ischemic and anti-hypoxic action by timed-release of the vasodilative component from the enterosoluble unit;
- the different colouring of the two complementary units, gastro- and enterosoluble, and the drug package in the form of calendar-blister, in usual conditions under silica gel protection or under vacuum package technology, ensures correctness, easiness, differentiation and evidence (daily, weekly, monthly) of the treatment and the suitable preservability of the drug;
- thanks to its dosage flexibility, it makes possible the differentiation of anti-stress and anti-impairment treatment depending on individual features and neuropsychic reactivity, as well as on obtaining at brain level mainly the anti-oxidative and anti-catabolic stress or anti-anabolic stress action;
- it offers the possibility to administer the drug by chronotherapeutic criteria (chronobiological posology).

BEST MODE FOR CARRYING OUT

Below are presented six examples of pharmaceutical production of the drug, according to this invention. For the purpose of controlled delivery in the release and absorption of the active substances, we established a selective formulation of the drug composition in two complementary units, gastro- and enterosoluble. The two complementary units are manufactured either in capsules, or in the form of film-coated tablets, and they are coloured differently for their identification in oral administration. In each of these examples are used the necessary quantities of active compounds and adjuvants in order to prepare 100 capsules or film-coated tablets.

The examples are given on illustrative purpose only and they do not limit in any way the scope of the invention.

EXAMPLE 1

| A) The composition for 100 gastrosoluble units is the following: | |
|---|---|
| - DL Methionine | 13.50 g |
| - Meclofenoxate hydrochloride (2-Dimethylamino)ethyl(p-chlorophenoxy)acetate hydrochloride | 24.00 g |
| - Zinc sulfate, anhydrous | 0.90 g |
| - Nicotinic acid with immediate-release | 0.90 g |
| - DL Aspartic acid · Mg salt, anydrous | 8.00 g |
| - D(-) Fructose | 0.90 g |
| - Vitamin $B_1$ hydrochloride | 0.70 g |
| - Vitamin $B_6$ hydrochloride | 1.00 g |
| B) The composition for 100 enterosoluble units is as follows: | |
| - Orotic acid, anhydrous (1,2,3,6-Tetrahydro-2,6-dioxo-4-pyrimidinecarboxylic acid) | 29.00 g |
| - di-Potassium hydrogen phosphate, anhydrous | 8.80 g |
| - Lithium carbonate | 0.20 g |
| - Nicotinic acid with prolonged-release | 7.00 g |
| - Magnesium oxide | 1.80 g |
| - Potassium iodide | 0.01 g |
| - D(-) Fructose | 0.90 g |

A minimum active anti-stress dose, for one day, consists in the administration of two gastrosoluble units and one enterosoluble unit.

A) The process for manufacturing the gastrosoluble unit. The above mentioned composition for 100 gastrosoluble units may be formulated in two preferable ways, namely: a mixture of granules and powders, or a film-coated tablet and powders.

a) The preparation of the mixture composed of granules of meclofenoxate and powders of the other active substances is performed in conformity with the physico-chemical properties of the active principles and using the method of successive dilutions, thus obtaining six mixtures (I-VI), as follows:

I 24.00 g meclofenoxate hydrochloride [20], over which 15.00 g isopropyl alcohol in thin film are poured, are granulated through the sieve 10 with medium thread and dried at 35° C. The granule thus obtained, after drying, is homogenized through the sieve 20, then are powdered with 0.277 g aerosil [90] and briquetted with a 9 mm diameter punch. The resulting briquette is grinded on the sieve 20;

II 0.90 g anhydrous zinc sulfate [20], 0.90 g D(-)fructose [20] are separately homogenized by mixing, then they are incorporated into the following mixture:

III made up of 0.90 g nicotinic acid [20], 0.70 g vitamin $B_1$ hydrochloride [20] and 1.00 g vitamin $B_6$ hydrochloride [20];

IV obtaining the mixture IV (IV=II+III);

V 24.277 g mixture I [20], 13.50 g DL methionine [20] and 8.00 g anhydrous DL aspartic acid-Mg salt, [20] are homogenized, forming a mixture;

VI in the previous mixture V, the mixture IV is progressively incorporated, and the whole is powdered with 0.549 g talc [90], thus resulting the final mixture VI (the composition for 100 gastrosoluble units).

The simple numbers or numbers in brackets represent the codes of German Standard Specifications of the sieves for each row material of pharmaceutical technologies.

b) The preparation of the mixture consisting in the meclofenoxate film-coated tablet and the powders of the other active substances is performed in two states. In the first step, the film-coated tablet of meclofenoxate is manufactured. After granulating the meclofenoxate, according to the technique described above, except the state of briquetting, it is compressed on a lenticular punch, 7 mm in diameter, and afterwards the tablet is coated with a gastrosoluble polymer film. The second step consists in the preparation of the other mixtures, according to the technique described under a).

For the pharmaceutical preparation of the active substances one may also use other known adjuvants that can achieve the technological and therapeutic purposes of the drug.

The gastrosoluble unit composition, prepared according to procedures a) or b), is encased in hard gelatin (operculated) capsules as follows:

a) the filling of capsules with granules and powders is performed in one stage, using a single dosage station (the one used for granules-powders), and is followed by their closing;

b) the filling of capsules with tablet and powders is performed in two states, using two successive dosage stations (one for tablets and the other for powders) and is followed by their closing. In both procedures, the operations of filling and closing the capsules are carried out automatically by filling and closing machines, in harmony with GMP (Good Manufacturing Practices) guidelines.

The gastrosoluble composition may also be encased in soft gelatin capsules.

Furthermore, for the pharmaceutical preparation of the gastrosoluble unit one may employ other procedures of production, like the compression of active substances and adjuvants, followed by the film coating of the tablet obtained with a gastrosoluble polymer in aqueous dispersion, for instance hydroxypropyl methylcellulose dispersion of 3 cP and 5–6 cP viscosity, methacrylic copolymer or a gastrosoluble polymer dissolved in an organic solvent, e.g. hydroxypropyl methylcellulose of 15 cP and 50 cP, 3 cP and 5–6 cP viscosity, methacrylic copolymer.

In all above mentioned cases, the gastrosoluble unit of drug (gastrosoluble capsule or film-coated tablet) is obtained, in conformity with the pharmaceutical requirements (Romanian Pharmacopoeia (RO. Ph. X), Xth ed., Medical Publishing House, Bucharest, 1993, in Romanian; European Pharmacopoeia (Eur. Ph.), 2nd ed., Maisonneuve, Sainte-Ruffine, vol. I, 1980 and vol. II, nos. 1–13, 1980–1990; The United States Pharmacopoeia (USP XXII), XXII rev., The United States Pharmacopeial Convention, Rockville Md., 1990; British Pharmacopoeia (BP 1988), vol. 1 and vol. 2, Her Majesty's Stationery Office, London, 1988).

The process for manufacturing the enterosoluble unit. The novelty of the process, according to the invention, consists in the production of an enterosoluble unit, being able to ensure controlled guidance in the release and absorption of the active substances, as well as the prolonged anti-ischemic and anti-hypoxic action. The two medical necessities are solved by the process, according to the invention, but the pharmaceutical technology is performed in reverse order. Thus, the new pharmaceutical process provides the timed-release of nicotinic acid as a vasodilative active principle and the enteric coating of capsules, after their filling and closing, resulting in their gastroresistance and enterosolubilization.

For retardation, the nicotinic acid is prepared either in the form of a prolonged-release granule, uniformly embedded in other powder mass, or as a prolonged-release tablet, introduced together with the rest of powders in a capsule.

a) In the following, the preparation of the composition for 100 enterosoluble units, with the timed-release granule of nicotinic acid is described. For retardation, in the first step ethyl cellulose as insoluble polymer and diethyl phthalate as plasticizer in a ratio (wt/wt) of 1/0.18–1/0.24 are used, and in the second step Carnauba wax as retarder is introduced in a ratio (wt/wt) of 1/0.47–1/0.53 to the first retarder. In preparing the content of capsules, achieved by the method of successive dilutions, four mixtures (I–IV) are obtained, as follows:

I over 7.000 g nicotinic acid [20], 0.430 g aerosil [90], 0.262 g polyvinylpyrrolidone [90] forming a homogeneous mixture, a solution of 4.080 g isopropyl alcohol, 3.000 g methylene chloride and 0.178 g diethyl phthalate in which 0.870 g ethyl cellulose was dissolved on a water bath, under stirring, is added in thin film. The mass thus obtained is granulated through the sieve 10 with medium thread, dried at 35° C., and then the granule is made uniform on the sieve 10 with medium thread. After that, a solution of 2.000 g isopropyl alcohol, 1.300 g methylene chloride, in which 0.434 g Carnauba wax was dissolved on a water bath, under stirring, is added. The mixture is granulated on the sieve 10 with medium thread, dried at 35° C., then uniformized on the sieve 10 with medium thread;

II 0.01 g potassium iodide [45], 0.001 g sodium thiosulfate [45], 0.20 g lithium carbonate [45] in a homogeneous mixture are incorporated in 0.90 g D(-) fructose [45];

III 1.80 g magnesium oxide [45] are added to the mixture II, then they are homogenized by repeated sifting through sieve 10;

IV in a homogeneous mixture of 29.00 g anhydrous orotic acid [20] with 8.80 g anhydrous dipotassium hydrogen phosphate [20], the mixture III is incorporated, then the mixture I is added, and finally is powdered with 0.2628 g aerosil [90]. Thus, the final mixture IV (the composition for 100 enterosoluble units) is obtained.

The simple numbers or numbers in brackets represent the codes of German Standard Specifications of the sieves for each row material of pharmaceutical tehnologies.

b) The manufacturing of the composition for 100 enterosoluble units, with the timed-release tablet of nicotinic acid takes place in two stages. The first step consists in obtaining the prolonged-release tablet by compressing the retarded granules of nicotinic acid according to the technique described above, on a lenticular punch, 6 mm in diameter. The second step consists in preparing the other mixtures according to the technique described under a).

The two modalities allow a differentiated timed-release of the nicotinic acid, during a period of about 2–3 hours in the case of procedure a) and in an interval of about 7–8 hours in the case of procedure b).

The composition of the enterosoluble unit, prepared by processes a) or b) is introduced into hard gelatin (operculated) capsules, in similar conditions as those described for filling and closing the gastrosoluble capsules.

The enterosoluble composition may be encased in soft gelatin capsules too.

As it was already mentioned above, another novelty of the process is the enteric coating of hard gelatin capsules. The preferred technology is the enteric coating in aqueous dispersion, because this is economic and at the same time conforms with antipolluant standards. The process of achieving the enteric coating is that of the fluidized bed, which allows the uniform coating of the capsules on their whole surface.

One of the preferred compositions of the enteric coating dispersion for 100 capsules is the following:

| - Cellulose acetate phthalate | 5.160 g |
|---|---|
| - Diethyl phthalate | 1.840 g |
| - 25% Ammonium hydroxide | 1.500 g |
| - Colorant | 0.006 g |

The enterosoluble polymer/plasticizer ratio (wt/wt) is 1/0.33–1/0.39, and the enterosoluble polymer/colorant ratio (wt/wt) is 1/0.0010–1/0.0012. Other compositions of the aqueous dispersion for enteric coating, used in the process according to the invention, may contain, instead of cellulose acetate phthalate other gastroresistant-enterosoluble polymers, like: polyvinyl acetate phthalate, hydroxypropyl methylcellulose phthalate, cellulose acetate trimethylate, methacrylic copolymer. Although it was indicated that, for enteric coating, aqueous dispersions of the above mentioned polymers are preferred, they can be used solved in organic solvents too. As plasticizer, instead of diethyl phthalate, one can also employ dibutyl phthalate, propylene glycol, triacetin. The plasticizers used improve flexibility and durability of the coating increase resistance to chipping or cracking and decrease the transmission of water vapours through this film. The economic, non-polluting process and the industrial equipment of good yield, accuracy and reproducibility used for enteric coating in aqueous dispersion, according to the present invention, fit the qualitative guidelines of GMP.

The enteric coating of the capsules is preferably performed on an equipment of intermittent film coating, which ensures the proper drying of the resulting film, and avoids any film irregularities, capsule adhesion or capsule diformity. Likewise, the enteric coating can also be made by means of a continous film coating instalation, taking into account that drying times have to increase in direct proportion to the thickness of the film, in order to obtain its optimum drying and uniformity. Due to the sensitivity of gelatin capsule wall to aqueous solutions, the coating procedure has two stages. The first consists in a pre-coating with a thin layer of enterosoluble polymer film, up to the weight of about 15–20 mg/capsule. In this phase a maximum air to a minimum polymer ratio in the aqueous dispersion must be maintained, to obtain the rapid drying of the film. The average temperature at which the coating takes place is 70° C. In the second state, using spraying, the gradual increase in the film thickness and weight is carried out, by changing the above mentioned ratio, meaning the increase of the polymer aqueous dispersion flow to the detriment of the air flow, concomitantly with the gradual increase in drying times, depending on the thickness of the film obtained. The second step lasts until reaching a weight of about 60–70 mg film/capsule. The optimum weight is established in accordance with the result of the disintegration test, according to Eur. Ph., 1980; gastroresistance≧2 hours, enterosolubilization≦1 hour.

Furthermore, for the pharmaceutical preparation of the enterosoluble unit one may employ other production processes, like the compression of the active substances after the retardation of nicotinic acid, using well-known adjuvants, followed by the film coating of the tablet thus obtained with a gastroresistant-enterosoluble polymer in aqueous dispersion or solved in an organic solvent.

In all above mentioned cases, the enterosoluble unit of the drug is obtained (enterosoluble capsule or film-coated tablet), which corresponds to the stipulations of RO. Rh. X, 1993, Eur. Ph., 1980, USP XXII, 1990, and BP, 1988.

EXAMPLE 2

A) The composition for 100 gastrosoluble units is the following:

| | |
|---|---|
| - DL Methionine | 16.50 g |
| - Meclofenoxate hydrochloride (2-(Dimethylamino)ethyl (p-chlorophenoxy)acetate hydrochloride) | 28.00 g |
| - Zinc sulfate, anhydrous | 1.20 g |
| - Nicotinic acid with immediate-release | 1.10 g |
| - DL Aspartic acid · Mg salt, anhydrous | 10.00 g |
| - D(-) Fructose | 1.10 g |
| - Vitamin $B_1$ hydrochloride | 0.90 g |
| - Vitamin $B_6$ hydrochloride | 1.20 g |

In this formulation, meclofenoxate hydrochloride may be replaced by meclofenoxate hybenzate, within the same limits.

B) The composition for 100 enterosoluble units is as follows:

| | |
|---|---|
| - Orotic acid, anhydrous (1,2,3,6-Tetrahydro-2,6-dioxo-4-pyrimidinecarboxylic acid) | 34.00 g |
| - di-Potassium hydrogen phosphate, anhydrous | 10.80 g |
| - Lithium carbonate | 0.30 g |
| - Nicotinic acid with prolonged-release | 9.00 g |
| - Magnesium oxide | 2.20 g |
| - Potassium iodide | 0.014 g |
| - D(-) Fructose | 1.10 g |

In this formulation, orotic acid may be used both in its anhydrous form and as monohydrate, within the same limits.

A minimum active anti-stress daily dose, consists in the administration of two gastrosoluble units and one enterosoluble unit.

The pharmaceutical technology of the two complementary units develops in accordance with the stages described in example 1.

EXAMPLE 3

A) Examples 1 and 2 not being limitedly, for manufacturing the gastrosoluble unit, out of the class of aminoethanol phenoxyacetates, the 24.00 g meclofenoxate hydrochloride may be replaced by 16.00 g meclosulfonate hydrochloride, as can be seen from this example, which also achieves the therapeutic purposes of the drug.

In this case, the composition for 100 gastrosoluble units is the following:

-L(-)Methionine 13.50 g target symptoms, each of them with 4 intensity degrees), 8 psychological tests (7 psychometric for attention, memory, general intellectual operativity, total average cognitive performance and one personality test), paraclinical investigation—bioelectric (EEG and ECG recordings) and biological-humoral (usual laboratory tests).

The therapeutic efficacy of the drug, according to the invention was very good and good, in both the neurasthenia disease and syndrome, as well as upon the neurasthenic in-patients and those still on their jobs; in the meantime the neuropsychic and somatic effects were maintained over the long term. No adverse reactions were registered. The therapeutic benefit obtained after 1–2 weeks of treatment (GORGOS, C., BOTEZAT-ANTONESCU, I., Results of clinical trial with Antagonic-Stress drug in neurasthenia, "Titan" University Polyclinic, "Titan" Mental Health Centre, Bucharest, 1988, in Romanian) was objectified clinically and paraclinically by:

a) quantitative and qaulitative regression and the disappearance of the symptomatology specific to neurasthenia, the normalization of the wakefulness-sleep biorhythm, the disappearance of neurovegetative troubles and of psychosomatic disorders; alongside with b) normalization of performances in the concrete activity, with the recovery of motivation and work capacity, accompanied by the increase of professional efficiency;

c) emotional stabilization (overall affective) and enhancement of the neuropsychic resistance to aggression by psychosocial stressors in case of continuing work in a stress-inducing environment;

d) regulation of cerebral electrogenesis, as a consequence of metabolic regulation and functional normalization of the nerve cells;

e) emphasizing the myocardial anti-ischemic, moderate hypotensive, hepatoprotective and normolipidemic effects in those patients who suffered from these disorders before treatment.

Clinical trial II. The therapeutic efficiency of the drug, acoording to the invention, in the treatment of chronic alcoholism Chronic alcoholism (ethanol dependence) was moderate and severe, the duration of addiction between 10 and 35 years, with neuropsychiatric and somatic impairment and negative psychosocial consequences.

The characteristics of the group investigated were: 30 in-patients, only males (since the frequency of heavy drinkers is 2–5 times higher in males than in females), aged between 31 and 59 (mean age—47 years). The homogeneity of this selected group was obtained by applying the criteria for inclusion and inside each of them the criteria for severity (anamnestic, psychiatric-psychological, psychosocial, somatic, screening tests, lack of therapeutic results through previous complex drugs and treatments), as well as of criteria for exclusion (American Psychiatric Association, Diagnostic and Statistical Manual of Mental Disorders (DSM-III-R), third edition, revised, American Psychiatric Association, Washington, D.C., 1987). The treatment with the anti-stress, anti-impairment and anti-aging drug was exclusive, in oral posology, for one month.

The assessment methodology, administered before, during and at the end of the treatment period, involved: psychiatric evaluation—interview-examination, the scale for chronic alcoholism evaluation (10 items), Hamilton depression scale (21 items); psychologic assessment—Bourdon- Anfimov, Herwig III, subtest COD from Wechsler Adult Intelligence Scale, Klazow, auditive Ray, Wechsler memory scale (M.Q.), Raven (I.Q.-matrix 1938, I list), Luscher; clinical evaluation—neurologic, ophthalmologic, of internal medicine; paraclinical assessment—bioelectric (EEG, ECG recordings), hematologic, metabolic, immunologic and screening tests.

The evident therapeutic value consisted in obtaining a rapid therapeutic benefit, which was constant, intense, multiple and persistent. No toxic effects and adverse reactions were noticed. The therapeutic benefit (PREDESCU, V., NEICU, N., STEFANESCU, P., PRELIPCEANU, D., ANDRUCOVICI, I. DAVID, E., VRABIE, E., ROMAN, I., SIMOCA, I., BUDILEANU, M., SIMA, I., NEGRU, T., DUMITRESCU, G., REU, G., Results of clinical trial with Antagonic-Stress drug in psychic impairments induced by constant alcohol consumption (chronic alcoholism, ethanol dependence), "Gh. Marinescu" Clinical Hospital, Department of Psychiatry, Bucharest, 1988, in Romanian), objectified through a complex clinical and paraclinical methodology, is the consequence of multiple actions of the drug and its effects:

a) psychotropic consequences—psychotonic of metabolic regulation, antidepressive, nootropic, sleep normalization, neuropsychic revitalization; remission, under treatment, of the withdrawal symptomatology, of the acquired dependence and tolerance; synergistic effect by increasing (normalization) and supporting the cognitive performances, concomitantly with the behaviour stabilization, in point of affective/emotional and relational/social, which enhance the resistance to effort and stressor aggression;

b) neurotropic effects—cerebral vasodilative, correction of the cerebral electrogenesis, regression up to disappearance of the signs and symptoms of alcohol toxicodeficiency encephalo-myelo-polyneuropathy;

c) somatotropic consequences—ocular—trophic and vasodilative action; hepatoprotective and anti-toxic—fast remission of the hepatic cytolytic and insufficiency syndroms; cardiovascular—improvement of myocardial irrigation, decrease of bioelectric signs from alcoholic myocardiopathy, disease also favorized by chronic cigarette smoking, moderate hypotensive effect; the general revitalization of the organism and anabolic stimulation;

d) hematologic effects—anti-anemic action, normalization of macrocytosis and of mild leukocytosis;

e) metabolic consequences—anabolic regeneration, hypolipidemic and hypoglicemic actions;

f) immunologic effects—immunostimulation by recovery of the humoral and cell-mediated immune deficiency.

Clinical trial III. The therapeutic efficiency of the drug, according to the invention, in the treatment of chronic cerebral circulatory insufficiency Out of the types of chronic cerebral circulatory insufficiency we chose the decompensations occurring in the vertebrobasilar territory, the patients having at the same time a fragile and deficient vascular system, a somatic background of biological impairment and aging and an organism that had been marked by stressors, risk factors and stress-related illnesses.

The characteristics of the group investigated were: 30 in-patients, of both sexes (11 males and 19 females), aged between 47 and 72 (mean age—59 years). The selected group was homogeneous thanks to the application of criteria for inclusion (positive diagnosis) and criteria for exclusion (differential diagnosis), (Organisation Mondiale de la Sante (OMS), Application a la Neurologie de la Classification Internationale des Maladies (CIM-AN), OMS, Geneve, 1989, in French). The treatment with the anti-stress, anti-impairment and anti-aging drug was exclusive, in oral posology, and lasted one month.

The assessment methodology, administered before, during and at the end of treatment period, involved: the neurologic examination card, the evaluation scale of chronic cerebral circulatory insufficiency (10 target symptoms, each of them with 4 intensity degrees), bioelectrical records (EEG, ECG), and biological-humoral investigation (laboratory tests).

The therapeutic efficacy of the drug, according to the invention, was very good (rapid, global and significant). No adverse reactions were registered. The therapeutic benefit (STAMATOIU, I., DIMITRIU, R., NICOLAE, I., Results of clinical trail with Antagonic-Stress drug in chronic cerebral circulatory insufficiency from vertebrobasilar territory, Clinical Hospital of Bucharest Municipality, Department of Neurology, Bucharest, 1988, in Romanian; POPA, C., MACOVEI, M., Results of clinical trial with Antagonic-Stress drug in chronic vertebrobasilar insufficiency, "Gh. Marinescu" Clinical Hospital, Department of Neurology, Bucharest, 1988, in Romanian), clinically and paraclinically objectified, confirmed the efficiency of the drug in cerebroprotection and in the treatment of brain aggression by ischemia, hypoxia, chronic stress and accelerated wear and tear, and consisted of:

a) the rapid regression of the neurologic and asthenic symptomatology, accompanied by the disappearance of symptoms;

b) the obvious improvement of cortical electrogenesis and the decrease down to disappearance of the bioelectric sign of myocardial ischemia;

c) obtaining a global biological response of neuropsychic revitalization (through cerebral vasodilative, nootropic and psychotonic metabolic effects) and somatic revitalization (through hepatoprotective, moderate antihypertensive and normolipidemic consequences, as well as by the synergism with hypoglycemic medication).

The versatile and superior therapeutic efficiency of the drug, according to the invention, emphasized by the three preclinical tests and the three clinical trials, was obtained thanks to the fact that the drug was developed in terms of a biological drug, as can be seen from the pharmaceutical examples, and due to its specific and synergistic anti-stress, anti-impairment and anti-aging actions.

Thus, the drug is a synergistic biological, neurometabolic and cell-trophic composition with active anti-stress principles (psychotropic, neurotropic, hepatotropic and myocardiotropic constituents), basic (normal) components of the biological systems and of the central nervous system, which pass through the blood-brain barrier, are actively and physiologically integrated in the biochemistry of neurons and neuroglias, specifically control the cerebral circulation and metabolisms. Being a biological drug, it is well accepted by the organism and is non-toxic, it produces no adverse reactions, tolerance and dependence, and it exhibits no danger of overdosage or intoxication; the drug itself has anti-toxic, detoxicant and homeostatic effects. Furthermore, the possibility appears to employ it in a long-term administration, as a drug for neuropsychic and biological support, for obtaining and consolidating the actions of vascular, energetic, polymetabolic and ultrastructural regulation of the brain, which are necessary in the conditions of magnifying and chronicization of stressors and intensification of neuropsychic-biological wear and tear.

The specific homeostatic and etio-pathogenic actions of the drug against stress, wear and tear and aging are achieved directly (primarily and secondarily) or as pro-drugs, through its active anti-stress components, with synergistic and polyvalent actions:
a) against oxidative and catabolic stress;
b) against anabolic stress;
c) vasodilative and normolipidemic;
d) energo-active; and
e) anti-toxic.

a) The components active against oxidative and catabolic stress of the anti-stress, anti-impairment and anti-aging drug, according to the invention, are: methionine, aminoethanol phenoxyacetates (meclofenoxate, meclosulfonate, eclofenoxate, adafenoxate) and/or aminoethyl phenoxyacetamides (mefexamide, fenoxedil, fexicaine, fipexide).

Methionine is a natural antioxidant, which antagonizes oxidative stress, through the biosynthesis of thiolic compounds, as well as catabolic stress, being a donor of methyl groups, metabolically sustaining against stress these biochemical reactions of the general adaptation syndrome.

Meclofenoxate is a biological compound, an organic ester, which is hydrolyzed in brain into two natural metabolic active substances: p-chlorophenoxyacetic acid, a phytohormone (auxin) and a cerebral modulator of neurotransmitters, and dimethylaminoethanol, a natural aminoalcohol, a precursor of brain acetylcholine and of cerebral lipids (phospholipids and sphingolipids).

The etio-pathogenic action of the active components against oxidative and catabolic stress is achieved by ensuring the metabolic support: the sustenance of anti-oxidant defence biological systems, the free radical scavenging ability, the antagonization of lipid peroxidation, polymerization and cross-linkages in macromolecules (antagonization the mechanisms of lipofuscin pigment formation and accumulation), lipofuscinolysis, re-balancing of the negative balances (thiolic, sulfur, methyl, choline, phosphatides) caused by stress, aging, hypoxia-ischemia and alcoholism in the organism and brain, the antagonization of excessive calcium accumulation in the brain (induced by the damage of cell membranes and free radical attack). In this way, the active principles against oxidative and catabolic stress effect also an anti-toxic action in the nervous system.

The specific action of constituents against oxidative and catabolic stress is amplified by the contribution of the other active principles of the drug according to the invention.

Thus, the compounds against anabolic stress act through orotic acid (lipofuscinolysis), piracetam (decreasing the quantity of cerebral nonesterified fatty acids, from the increased amount due to stress), zinc (anti-oxidant), lithium (anti-catabolic), whereas the whole class operates through anabolic regeneration, which opposes catabolism, and degradation.

The vasodilative and normolipidemic components act through nicotinamide (which diminishes the cerebral nonesterified fatty acids, existing in increased amount due to stress) and through the antagonization of hypoxic-ischemic stress and of chronic alcoholism, which cause lipofuscin pigment accumulation in the brain.

In their turn, the anti-toxic constituents support the homeostatic action of the active principles against oxidative and catabolic stress, by detoxifying and elimination of the catabolism products at structural, metabolic and molecular level in the nervous tissue.

Thus, the active principles against oxidative and catabolic stress are geroprotective agents, because they decelerate subcellular wear and tear and aging processes in the brain, which is the tissue having increased fragility to oxidative stress and free radical attack.

The therapeutic efficiency of the drug according to the invention in antagonization of the oxidative and catabolic stress was demonstrated at the nervous level: by protection, stabilization and increasing the resistance of neuronal and glial membranes (in animal psychic stress); neurobiochemically by protecting cerebral macromolecules and diminishing the number of cross-linkages in protein macromolecules; also neuromorphologically (by light, fluorescence and electron microscopy), based on the action against lipofuscin formation, neuronal and glial lipofuscinolysis and that of lipofuscin elimination (in animal chronic alcoholism and aging). The homeostatic action against oxidative and catabolic stress was clinically objectified in the treatment of chronic alcoholism, by the remission of the hepatic and pancreatic cytolytic (hypercatabolic) syndrome, and by the rapid, functional and metabolic normalization of the liver.

b) The components active against anabolic stress of the anti-stress, anti-impairment and anti-aging drug, according to the invention, are: hydrooxopyrimidine carboxylates (orotic acid and orotates of the drug bioelements) and/or oxopyrrolidine acetamides (piracetam, oxiracetam, etiracetam, dimethylphenyl piracetam, pramiracetam, aniracetam) associated with potassium, zinc and lithium.

Orotic acid (vitamin $B_{13}$) has an intense action of anabolic regeneration, because it is the natural metabolic precursor common for pyrimidine nitrogenous bases (uracil, cytosine, thymine, 5-methylcytosine) from nucleic acids (DNA, RNA) and macro-ergic pyrimidine nucleotides (UTP, CTP, TTP), or from the composition of coenzymes (UDPglucose, UDPgalactose, CDPcholine), which interfere with carbohydrate and lipid metabolisms: these, alongside protein and nucleic acid metabolisms, are extremely important in the brain. Thus, orotic acid has a lipotropic effect, stimulating the phospholipid synthesis and also increasing the glycogen synthesis in hepatic, myocardial and nerve cells, and through enhancing RNA synthesis in brain it provides the subcellular and metabolic support for the long-term memory. Therefore, orotic acid represents a strong natural anabolic and biological support for the brain, liver and myocardium.

Piracetam activates the biosynthesis of cerebral macromolecules (RNA, proteins) and lipids, especially in post-hypoxic recovery and in old animals, where it promotes polyribosome synthesis and their extension, by providing the energy transfer between the systems which produce energy and those which use it (cellular anabolism, subcellular regeneration).

Potassium, zinc, lithium and the other neuroactive bioelements of the drug according to the invention (magnesium, iodine, monoacid phosphate, sulfate) are intracellular cations and anions, mono- and divalent, essential for living matter. They play structural (plastic) and metabolic (dynamic) roles, and are involved in fundamental biocatalytic systems for the functional adaptation of the cell—enzymes, hormones, vitamins and macro-ergic compounds. They acquire specific functions in nerve cell metabolism and physiology: in neurotransmitter activity, in excitation-inhibition processes, in nerve conduction and axoplasmic transport, in memory and neurosecretion. They exhibit a negative balance in stress-impairment, chronic alcoholism, hypoxia-ischemia, especially magnesium, zinc, sulfate, and iodine. Magnesium is a subcellular stabilizer, lithium a humoral stabilizer, and the limbic system displays increased sensitivity to this bioelement, while zinc has an increased concentration in hippocampus.

The therapeutic efficiency of active compounds against anabolic stress is sustained also by other active principles of the drug, according to the invention, as already mentioned above for the other bioelements, taking into account the dependence of cerebral anabolism on the cerebral blood flow and on the nervous energy metabolism.

Thus, the components against oxidative and catabolic stress act through methionine and aminoethanol phenoxyacetates. In the brain, the methyl groups supplied by methionine are intensely consumed in the anabolism processes of neurotransmitters, in cerebral lipid biosynthesis and in the post-transcriptional methylation of the nervous macromolecules—nucleic acids and proteins. Meclofenoxate promotes the synthesis of cerebral RNA and macro-ergic nucleotides, and, through its hydrolysis compound (dimethylaminoethanol), it contributes in the same way as meclosulfonate, to the cerebral phospholipid synthesis.

The active vasodilative components (against hypoxic-ischemic stress) provide the contribution of nutrients, which are necessary to anabolic regeneration and to antagonization of anabolic stress-inducing processes (hypoxic-ischemic stress).

The energo-active compounds: aspartate (precursor in the biosynthesis of purines and pyrimidines), fructose, vitamin $B_1$, vitamin $B_6$ and monoacid phosphate create the energetic support necessary for intensifying anabolism.

The therapeutic efficacy of the drug according to the invention in antagonizing anabolic stress, in chronic alcoholism and nervous wear and tear, and the intense functional and ultrastructural anabolic activation and regeneration of nerve cells were demonstrated on animal brain, neurobiochemically, by enhancing the amounts of RNA, total proteins and water soluble proteins, as well as neuromorphologically (light and electron microscopy), by neuronal repopulation with Nissl bodies, rough endoplasmic reticulum and free ribosomes. Anabolic regeneration was clinically emphasized in the treatment of chronic alcoholism by remission of hepatic insufficiency and immune deficiency, by the anti-anemic effect and weight regain.

c) The active vasodilative (against hypoxic-ischemic stress) and normolipidemic components of the anti-stress, anti-impairment and anti-aging drug, according to the invention, are: nicotinic alcohol and/or acid or its deriatives (nicotinamide, magnesium nicotinate) associated with magnesium and iodine.

They operate etio-pathogenically by increasing the cerebral blood flow, enhancing the permeability of the blood-brain barrier and the transport of glucose, by improving the nerve and myocardial cell supply with anabolites and their purification of catabolites. These compounds produce an antispastic, spasmolytic action, physiologic cerebral vasodilatation (primary—vasculotropic) and a natural anti-hypoxic and anti-ischemic protection of the brain. Furthermore, they act as normolipidemic and lipid homeostatic agents, by decreasing the high levels of triglycerides, total cholesterol, VLDL cholesterol (very low-density lipoprotein cholesterol), LDL cholesterol (low-density lipoprotein cholesterol), and by increasing the low levels of HDL cholesterol (high-density lipoprotein cholesterol). In its turn, the normolipidemic action exerts positive effects on cerebral vasodilatation.

Moreover, the therapeutic efficiency of vasodilative and normolipidemic components is also based on the action of the other active substances of the drug, according to the invention. The active principles against oxidative and catabolic stress, those against anabolic stress and the energo-active ones operative as psychotropic-psychotonic compounds for metabolic regulation, and thus they produce a secondary cerebral vasodilatation—a neuromerometabolic one, which is subsequent to the functional and metabolic cerebral stimulation. The active components against oxidative and catabolic stress, orotates and potassium belonging to constituents against anabolic stress, and aspartates, fructose, vitamin $B_1$, vitamin $B_6$ belonging to energo-active principles, antagonize the hypoxic-ischemic stress. Orotic acid, meclofenoxate, meclosulfonate and methionine act as blood normolipidemic agents, also through intensifying the intracellular lipid synthesis at hepatic, cerebral and myocardial levels or due to a choleretic effect (by magnesium and orotic acid).

The vasoactive components of the drug, according to the invention, without retarded delivery in the gastrosoluble unit and with prolonged delivery in the enterosoluble one, provide both a rapid vasodilatation and one prolonged, over a long period (about 2–3 hours in case of the prolonged-release granule, and about 8 hours in case of the prolonged-release tablet), which are necessary in the control of hypoxia-ischemia induced by stress, impairment and normal and pathological aging. The concomitant administration of the two complementary units achieves sustained vasodilatation (immediate+prolonged), necessary in cerebral and myocardial ischemic pathology.

The vasodilative action of the drug according to the invention may be enhanced by replacing, in the formulation of gastrosoluble unit, aminoethanol phenoxyacetates (base esters) by aminoethyl phenoxyacetamides (stabler amides), and among them, fenoxedil, a cerebral and peripheric vasodilator (based on vasculotropic-musculotropic mechanism) and psychotonic for metabolic regulation (vasodilatation through neurometabolic activation) is preferred.

The therapeutic efficiency of the drug according to the invention in antagonizing hypoxic-ischemic stress and in dyslipidemias was clinically emphasized in the treatment of chronic cerebral circulatory insufficiency, by the remission of ischemic symptomatology, by ophthalmologic positive effects, by cerebral and myocardial electrogensis correction, and in the treatment of chronic alcoholism by the normalization of the lipid profile and ocular positive effects.

d) The energo-active components of the anti-stress, anti-impairment and anti-aging drug, according to the invention, are: aspartate, D(-) fructose, vitamin $B_1$, vitamin $B_6$, monoacid phosphate, which support the energy metabolism of the nerve cell, overstrained and energetically exhausted during stress and impairment.

Aspartic acid—a gluco-formative amino acid, in a 96 $\mu$mol/100 g nervous tissue concentration, stored in the brain in its deposit form, namely N-acetylaspartic acid in a 490 $\mu$mol/100 g nervous tissue concentration—supplies energy by its metabolization in tricarboxylic acid cycle and GABA shunt (extremely intense in the brain); it is also an excitatory neurotransmitter and achieves a mobile connection between carbohydrate, energy, nucleic acid and protein metabolisms from the nerve cell.

D(-) fructose, a natural monosaccharide, which is metabolized independently of the insulin pathway, enhances the hepatic glycogen reserve or is rapidly integrated in the form of monophosphoric ester (D(-)fructose-6-phosphate) in the pentose phosphate shunt (oxidative degradation used by the nerve cells) or in the anaerobic glycolysis.

Vitamin $B_1$, vitamin $B_6$ and vitamin PP (nicotinamide), the last belonging to the vasodilative component, are exogenous biocatalysts, absolutely necessary for life and for the normal unfolding of the nervous functions. In their form of phosphoric acid esters (thiamine pyrophosphate and pyridoxal 5-phosphate) or of nucleotides (nicotinamide monoor dinucleotides), they represent the coenzymes (prosthetic group) for numerous essential enzymes, which interfere in energy, carbohydrate, protein and lipid metabolisms. Because of the increased intensity of cerebral metabolisms, the nervous system concentrates these vitamin in different zones and it is sensitive to their imbalances: negative balance determined by stress, wear and tear, aging and toxico-deficiency induced by chronic alcoholism. Vitamin $B_1$ is essential to the metabolization of lactic acid, pyruvic acid and in tricarboxylic acid cycle, and vitamin $B_6$ to activating the GABA shunt, thus being nervous metabolic pathways to stress antagonization.

The monoacid phosphate represents the support, a metabolic reserve in energy metabolism, and it is employed in glucide phosphorylation—for their entering in carbohydrate metabolism; in vitamins $B_1$, $B_6$, PP phosphorylation— in order to activate them as coenzymes; and for the synthesis of macro-ergic compounds—ATP, UTP etc.—for energy storage.

The therapeutic efficacy of the energo-active components is sustained by the action of other active principles of the drug, according to the invention, which interfere homeostatically in the main stages of the cerebral carbohydrate and energy metabolisms.

Thus, the constituents active against oxidative and catabolic stress act through aminoethanol phenoxyacetates, which enhance the glucose and phosphate transfer from blood into brain, the oxidative degradation of glucose through the pentose phosphate shunt, the strong exergonic cycle of tricarboxylic acids, the oxygen utilization by the nerve cell; they also act through the aminoethyl phenoxyacetamides that achieve a strong energo-active, psychoenergizing action; through methionine they act indirectly, contributing to biological methylation (synthesis of adrenaline, acetylcholine and creatine).

The compounds active against anabolic stress operate through orotic acid, which saves energy during the direct synthesis of pyrimidine nitrogenous bases, of the coenzymes and of macro-ergic compounds with uracil, during the re-synthesis of glycogen stocks and by piracetam, which stimulates the energy producing systems, increases the glucose consumption, the aerobic glycolysis, the ATP synthesis at the brain level and the "in vitro" respiratory coefficient of the mitochondrion (the subcellular organelle responsible for ATP biosynthesis); and through potassium and zinc, which interfere in many enzymatic reactions accompanied by release of energy.

The vasodilative components (against hypoxic-ischemic stress) act by the enhancement of the anabolite and oxygen amounts in the brain; through nicotinamide, a precursor in the NAD and NADP coenzyme synthesis, playing an important role in the cellular oxidation-reduction processes, through magnesium which interferes directly in many exergonic reactions, in the biosynthesis of macro-ergic compounds, in oxidative phosphorylation; and through iodine which produces a general metabolic activation, mainly in the brain, and which is particularly high in the hypothalamus and also accumulates in the spinal cord and medullas oblongata.

The association of energo-active neurometabolic components with those for nootropic-psychotonic of metabolic regulation (aminoethanol phenoxyacetates, aminoethyl phenoxyacetamides, hydrooxopyrimidine carboxilates and/or oxopyrrolidine acetamides), with methyl group donors (methionine, pramiracetam) and with physiologic cerebral vasodilative substances (having a rapid and prolonged action) psychically creates a psychoenergizing (antiasthenic) effect, the promotion of cognitive performances (attention, memory, intellectual promptness), an antidepressant effect, higher resistance to stress, wear and tear, hypoxia, and the normalization of cerebral electrogensis. These effects have been clinically proved in the treatment of neurasthenia, chronic alcoholism and chronic cerebral circulatory insufficiency, by using the drug, according to the invention.

e) The anti-toxic components of the anti-stress, anti-impairment and anti-aging drug, according to the invention, operate etio-pathogenically against hypercatabolic and toxic and deficient states, connected with the oxidative stress and the accumulation of endogenous toxic compounds, induced at ultrastructural and metabolic level of stress and impairment, hypoxia-ischemia, chronic alcoholism and aging.

In this way the metabolic detoxifying processes are activated, which in their turn:

diminish the number of the free radicals generated by oxidative stress through aminoethanol phenoxyacetates, methionine, orotic acid and zinc;

remove acidosis and cellular hypoxidosis, caused by the accumulation of lactic and pyruvic acids consequent upon oxidative stress, glucide hypercatabolism, thiamine-carbohydrate imbalance, hypoxia-ischemia, alcoholism through aminoethanol phenoxyacetates, orotic acid, potassium, zinc, magnesium, vitamin $B_1$ and vitamin $B_6$;

remove ammonia generated in excess through protein catabolism by aspartic acid—through the urea cycle, by transamination—together with vitamin $B_6$, asparagine and magnesium;

intervene in sulfoconjugation by methionine and sulfate, in glucurono-conjugation by fructose, in methylation by methionine and pramiracetam;

antagonize the excessive accumulation of calcium in the brain by aminoethanol phenoxyacetates.

They subcellular detoxifying processes are also activated, and they:

diminish the number of cross-linkages which make proteins-enzymes insoluble and inactive;

decrease the lipid peroxidation determined by oxidative and catabolic stress, acting against lipofuscinogenesis, by lipofuscinolysis and lipofuscin elimination.

Methionine, an essential amino acid, a natural detoxicant and lipotropic, a source for sulfur, a metabolic donor of methyl groups, and a precursor of SH and sulfate groups, plays a complex role in the anti-toxic action, thus being an important metabolic support for the anti-toxic and detoxifying activity.

The oral administration of the drug, according to the invention offers the advantages of direct anti-toxic and hepatoprotective actions and of actively sustaining the hepatic metabolic detoxifying processes, taking into consideration the central role played in these processes by the liver. The fact has been clinically proved in the treatment of chronic alcoholism by using this drug.

The cumulation of anti-toxic (metabolic—ultrastructural), vasodilative (anti-hypoxic, anti-ischemic, spasmolytic) and anabolic regeneration (subcellular—functional) actions with those against oxidative hypercatabolic stress (removal of neuronal lipid peroxides) and energo-active actions leads, at the plastic and functional level, to the trophic action (nervous, hepatic, myocardial) and to the neuropsychic and biological revitalization of the drug, according to the present invention.

INDUSTRIAL APPLICABILITY

The therapeutic indications of the drug, according to the invention result from:
- its integration into the fundamental processes of neurons and neuroglias and their support based on the biological, neurometabolic and cell-trophic composition;
- maintaining and increasing of the adaptive capacity and the neuropsychic and biological resistance by polymetabolic regulation and subcellular regeneration, first of all for nerve, hepatic and myocardial cells;
- the simultaneous achievement of brain, liver and heart protection from the incapacitation caused by acute and chronic stress, from cerebral impairment and the acceleration of aging, by homeostatic intervention at brain and body level;
- the correction of the main metabolic and ultrastructural imbalances brought about by stress, prolonged biological wear and tear and stress-related illnesses, thanks to its vasoactive, energo-active, anti-toxic actions and influences on catabolic regulation and anabolic regeneration;
- the complex, etio-pathogenic, anti-stress, anti-impairment, anti-ischemic, anti-hypoxic and anti-toxic involvement of the drug, based on its synergistic biological-metabolic composition (nootropics-psychotonics, vasodilators, energoactivators, stimulants of protein and nucleic acid synthesis, amino acids, vitamins and bioelements).

The administration of the drug, according to the present invention, to healthy humans (in harmony with the health promotion conception—preventive medicine) has the following effects:
- it elevates the general vitality of the organism, consolidates the neuropsychic tonus;
- it enhances the capacity for psychic and physical efforts, for the intellectual and sportive efficiency and performances;
- it increases the neuropsychic and biological adaptive capacity;
- it expands the resistance to overstrain, stress and impairment;
- it determines the fast recovery in cases of fatigue, exhaustion, overwork, after prolonged efforts or sleeplessness;
- it strongly decelerates brain and body wear and tear and promotes the extension of the functional life span, and of longevity, thus preventing impairment, involution, presclerosis and atherosclerosis;
- its suited for an extensive use, for the whole range of ages (children, young people, adults, old people), being especially indicated for people over 35–40 (when the adaptive capacity and resistance start decreasing progressively and continuously) and more specifically in performant activities or those having a high stressing and aggressive coefficient (management personnel, students, sportsmen, pilots, teams of space flights and missions etc.).

Since brain stimulation is achieved by ultrastructural, energetic and metabolic regulation, the administration of the drug according to the invention is not accompanied by depression, nervous exhaustion, tolerance, psychological and physical dependence; on the contrary an intense, strengthening, neuropsychic and general effect is obtained for over the long term.

The drug, according to the invention, is administered to sick persons for therapeutic and recovery purposes, increasing the daily active dose, depending on the nature and seriousness of the disease and on the characteristics of each patient. Thanks to its dosage flexibility, the drug is employed in stress-dependent, psychiatric and neurologic pathology, in geriatrics and internal medicine, in cases of:
- states of neuropsychic overstrain, maladaptive reactions to stress, acute and chronic psychosocial stress;
- states of exhaustion and biological stress determined by consumptive and hypercatabolic diseases, convalescence etc.;
- neurotic disorders: attention and memory disturbances, concentration troubles, the decline of intellectual efficiency; lower effort capacity, physical and psychic asthenia, overwork, exhaustion, sleep disorders; neurovegetative troubles, emotional lability, depression;
- stress-related disorders and stress-related illnesses: ischemic heart diseases, moderate arterial hypertension; hepatic insufficiency, chronic pancreatopathy; dyslipidemia; as adjuvant therapy in diabetes mellitus and its complications;
- psychogenic sexual dysfunctions: impotence, frigidity etc.;
- dysendocrine states by disturbances of hypothalamo-hypophysial complex, in menopause and andropause;
- cerebral toxic pathology: acute and chronic alcoholism (alcohol abuse and dependence, withdrawal syndrome, psychic and neurologic impairments due to alcoholism, detoxification cures); abuse and dependence on other psychoactive substances; intoxications with carbon monoxide or organic solvents;
- chronic cerebral circulatory insufficiency and other forms of cerebral vascular pathology: hypoxic, ischemic, thromboembolic, atherosclerotic;
- neuropsychic troubles caused by head trauma, post-traumatic stress disorders;
- involutive syndromes during pre-senescence and senescence: poor resistance to stress, physical and psychic tiredness, attention and memory deficiences, cognitive impairments, emotional lability, depression, diminishing of the adaptive capacity etc.

The administration of the drug, according to the invention, increases the social adaptive capacity, which has been decreased by stress, stress-related disorders and illnesses, psychiatric and neurologic diseases or in senescence, due to its therapeutic actions of behavioural and emotional-affective stabilization and of supporting the cognitive functions.

TABLE 1

Neuro-psycho-biological and etio-pathogenic-therapeutic trivalent experimental pattern for the application and checking-up of the anti-stress, anti-impairment and anti-aging drug, in accordance with this invention

| Stress etiologies Group types | 1. PSYCHIC stress (P.S.) by chronic painful emotion) | 2. BIOLOGICAL stress (B.S.) (by chronic alcohol intoxication) | 3. GLOBAL stress (G.S.) (by chronologically accumulated wear and tear) |
|---|---|---|---|
| I. NORMAL GROUP (healthy brains) | age: 8–9 months; methodologies: a. cell isolation b. neuromorphology c. neurobiochemistry no. of animals: a. 30 rats b. 10 rats c. 20 rats | age: 8–9 months; methodologies: a. cell isolation b. neuromorphology c. neurobiochemistry no. of animals: a. 30 rats b. 30 rats c. 120 rats | age: 8–9 months; methodologies: a. cell isolation b. neuromorphology c. neurobiochemistry no. of animals: a. 60 rats b. 90 rats c. 90 rats |
| II. INCAPACITATED GROUP (cronically stressed brains) | age: 8–9 months+ P.S.; methodologies: a. cell isolation b. neuromorphology c. neurobiochemistry no. of animals: a. 40 rats b. 20 rats c. 20 rats | age: 8–9 months+ B.S.; methodologies: a. cell isolation b. neuromorphology c. neurobiochemistry no. of animals: a. 40 rats b. 30 rats c. 120 rats | age: 24–26 months (G.S.); methodologies: a. cell isolation b. neuromorphology c. neurobiochemistry no of animals: a. 80 rats b. 90 rats c. 90 rats |
| III. REVITALIZED GROUP (anti-stress, anti-impairment and anti-aging recapacitated brains) | age: 8–9 months+ anti-P.S. tr. + P.S.; methodologies: a. cell isolation b. neuromorphology c. neurobiochemistry no. of animals: a. 40 rats b. 20 rats c. 20 rats | age: 8–9 months+ B.S. + anti-B.S. tr.; methodologies: a. cell isolation b. neuromorphology c. neurobiochemistry no. of animals: a. 40 rats b. 30 rats c. 120 rats | age: 24–26 months (G.S.) + anti-G.S. tr.; methodologies: a. cell isolation b. neuromorphology c. neurobiochemistry no. of animals: a. 80 rats b. 90 rats c. 90 rats |
| Partial sum TOTAL | 220 animals | 560 animals 1540 animals | 760 animals | anti-P.S. treatment and P.S.: daily, for 2 weeks;
B.S. and anti-B.S. treatment: daily, for 2 months;
G.S. (wear and tear accumulated gradually over 17 months) and anti-G.S. treatment: daily, for 2 months.
no.: number;
tr.: treatment.

TABLE 2

Results of nucleic acid assays (60 animals/group) and protein assays (60 animals/group) from the brains (telencephalon and diencephalon) of normal rats (age: 8–9 months), incapacitated by biological stress (chronic alcohol intoxication) and therapeutically revitalized with anti-stress, anti-impairment and anti-aging drug, in accordance with this invention.

| Brains (groups) Informational macromolecules | Normal (age: 8–9 months) ($\bar{x} \pm$ S.D.) | Incapacitated by biological stress ($\bar{x} \pm$ S.D.) | Therapeutically revitalized (recapacited) ($\bar{x} \pm$ S.D.) | Efficiency of revitalization |
|---|---|---|---|---|
| 1. Total DNA (mg/g wet sb.) significance | $1.361 \pm 0.098$ | $1.276 \pm 0.107$ incapacitation (−)0.085 mg (−)6.3% $p < 0.001$ | $1.33 \pm 0.100$ recapacitation (+)0.055 mg (+)4.1% $p < 0.01$ | 64.7% |
| 2. Total RNA (mg/g wet sb.) | $2.609 \pm 0.117$ | $1.884 \pm 0.114$ incapacitation (−)0.725 mg (−)27.8% | $2.502 \pm 0.122$ recapacitation (+)0.618 mng (+)23.7% | |

TABLE 2-continued

Results of nucleic acid assays (60 animals/group) and protein assays (60 animals/group) from the brains (telencephalon and diencephalon) of normal rats (age: 8–9 months), incapacitated by biological stress (chronic alcohol intoxication) and therapeutically revitalized with anti-stress, anti-impairment and anti-aging drug, in accordance with this invention.

| Brains (groups) Informational macromolecules | Normal (age: 8–9 months) ($\bar{x}$ ± S.D.) | Incapacitated by biological stress ($\bar{x}$ ± S.D.) | Therapeutically revitalized (recapacited) ($\bar{x}$ ± S.D.) | Efficiency of revitalization |
|---|---|---|---|---|
| significance | $p < 0.001$ | | $p < 0.001$ | 85.2% |
| 3. TP (mg/g wet sb.) | 98.61 ± 2.22 | 83.40 ± 2.23 incapacitation (−)15.21 mg (−)15.4% | 95.45 ± 2.39 recapacitation (+)12.05 mg (+)12.2% | |
| significance | $p < 0.001$ | | $p < 0.001$ | 79.2% |
| 4. WIP (mg/g wet sb.) | 23.92 ± 0.72 | 30.15 ± 1.51 incapacitation (+)6.23 mg (+)20.7% | 25.84 ± 0.81 recapacitation (−)4.31 mg (−)14.3% | |
| significance | $p < 0.001$ | | $p < 0.001$ | 69.2% |
| 5. WSP (mg/g wet sb.) | 74.58 ± 1.85 | 53.09 ± 1.59 incapacitation (−)21.49 mg (−)28.8% | 69.56 ± 1.41 recapacitation (+)16.47 mg (+)22.1% | |
| significance | $p < 0.001$ | | $p < 0.001$ | 76.6% | wet sb.: wet substance;
TP: total proteins;
WIP: water insoluble proteins;
WSP: water soluble proteins;
for indicators nos. 1, 2, 3 and 5 normal brains = 100%;
for indicator no. 4 incapacitated brains = 100%.

TABLE 3

Results of the calculated indicators derived from the ratios between informational macromolecules, extracted from the brains (telencephalon and diencephalon) of normal rats (age: 8–9 months), incapacitated by biological stress (chronic alcohol intoxication) and therapeutically revitalized with anti-stress, anti-impairment and anti-aging drug, in accordance with this invention.

| Brains (groups) Informational macromolecules | Normal (age: 8–9 months) ($\bar{x}$ ± S.D.) | Incapacitated by biological stress ($\bar{x}$ ± S.D.) | Therapeutically revitalized (recapacited) ($\bar{x}$ ± S.D.) | Efficiency of revitalization |
|---|---|---|---|---|
| 1. RNA/DNA ($\mu g/\mu g$) | 1.919 ± 0.095 | 1.485 ± 0.072 incapacitation (−)0.434 (−)22.6% | 1.880 ± 0.084 recapacitation (+)0.395 (+)20.6% | |
| significance | $p < 0.001$ | | $p < 0.001$ | 91.0% |
| 2. DNA/TP ($\mu g/mg$) | 13.787 ± 0.771 | 15.227 ± 0.949 incapacitation (+)1.440 (+)9.5% | 13.922 ± 0.805 recapacitation (−)1.305 (−)8.6% | |
| significance | $p < 0.001$ | | $p < 0.001$ | 90.6% |
| 3. RNA/TP ($\mu g/mg$) | 26.413 ± 0.945 | 22.568 ± 0.998 incapacitation (−)3.845 (−)14.6% | 26.197 ± 0.822 recapacitation (+)3.629 (+)13.7% | |
| significance | $p < 0.001$ | | $p < 0.001$ | 94.4% |
| 4. (WIP/TP) ×100 (%) | 24.3 ± 0.7% | 36.2 ± 1.8% incapacitation (+)11.89 (+)32.9% | 27.1 ± 0.9% recapacitation (−)9.08 (−)25.1% | |
| significance | $p < 0.001$ | | $p < 0.001$ | 76.4% |

TP: total proteins;
WIP: water insoluble proteins;
WSP: water soluble proteins;
for indicators nos. 1 and 3 normal brains = 100%;
for indicators nos. 2 and 4 incapacitated brains = 100%.

TABLE 4

Results of the nucleic acid assays (60 animals/group) and protein assays (30 animals/group) from the brains (telencephalon and diencephalon) of normal rats (age: 8–9 months), incapacitated by global stress (wear and tear accumulated gradually over 17 months) and therapeutically revitalized with anti-stress, anti-impairment and anti-aging drug, in accordance with this invention.

| Brains (groups) Informational macromolecules | Normal (age: 8–9 months) ($\bar{x} \pm$ S.D.) | Incapacitated by global stress ($\bar{x} \pm$ S.D.) | Therapeutically revitalized (recapacited) ($\bar{x} \pm$ S.D.) | Efficiency of revitalization |
|---|---|---|---|---|
| 1. Total DNA (mg/g wet sb.) | $1.372 \pm 0.121$ | $1.328 \pm 0.100$ incapacitation (−)0.044 mg (−)3.2% | $1.353 \pm 0.102$ recapacitation (+)0.025 mg (+)1.8% | |
| significance | $p < 0.05$ | $p > 0.05$ (NS) | 56.8% |
| 2. Total RNA (mg/g wet sb.) | $2.670 \pm 0.114$ | $2.192 \pm 0.123$ incapacitation (−)0.478 mg (−)17.9% | $2.584 \pm 0.121$ recapacitation (+)0.392 mg (+)14.7% | |
| significance | $p < 0.001$ | $p < 0.001$ | 82.0% |
| 3. TP (mg/g wet sb.) | $100.22 \pm 2.14$ | $88.48 \pm 2.01$ incapacitation (−)11.74 mg (−)11.7% | $96.20 \pm 2.02$ recapacitation (+)7.72 mg (+)7.7% | |
| significance | $p < 0.001$ | $p < 0.001$ | 65.8% |
| 4. WIP (mg/g wet sb.) | $24.72 \pm 1.13$ | $30.41 \pm 1.12$ incapacitation (+)5.69 mg (+)18.7% | $27.85 \pm 0.76$ recapacitation (−)2.56 mg (−)8.4% | |
| significance | $p < 0.001$ | $p < 0.001$ | 45.0% |
| 5. WSP (mg/g wet sb.) | $75.39 \pm 1.39$ | $57.85 \pm 1.83$ incapacitation (−)17.54 mg (−)23.3% | $68.48 \pm 1.18$ recapacitation (+)10.63 mg (+)14.1% | |
| significance | $p < 0.001$ | $p < 0.001$ | 60.6% | wet sb.: wet substance;
TP: total proteins;
WIP: water insoluble proteins;
WSP: water soluble proteins;
for indicators nos. 1, 2, 3, and 5 normal brains = 100%;
for indicator no. 4 incapacitated brains = 100%.

TABLE 5

Results of the calculated indicators derived from the ratios between informational macromolecules, extracted from the brains (telencephalon and diencephalon) of normal rats (age: 8–9 months), incapacitated by global stress (wear and tear accumulated gradually over 17 months) and therapeutically revitalized with anti-stress, anti-impairment and anti-aging drug, in accordance with this invention.

| Brains (groups) Informational macromolecules | Normal (age: 8–9 months) ($\bar{x} \pm$ S.D.) | Incapacitated by global stress ($\bar{x} \pm$ S.D.) | Therapeutically revitalized (recapacited) ($\bar{x} \pm$ S.D.) | Efficiency of revitalization |
|---|---|---|---|---|
| 1. RNA/DNA ($\mu g/\mu g$) | $1.944 \pm 0.078$ | $1.656 \pm 0.041$ incapacitation (−)0.288 (−)14.8% | $1.917 \pm 0.065$ recapacitation (+)0.261 (+)13.4% | |
| significance | $p < 0.001$ | $p < 0.001$ | 90.6% |
| 2. DNA/TP ($\mu g/mg$) | $13.723 \pm 0.771$ | $14.965 \pm 0.799$ incapacitation (+)1.242 (+)8.3% | $14.022 \pm 0.788$ recapacitation (−)0.943 (−)6.3% | |
| significance | $p < 0.001$ | $p < 0.001$ | 75.9% |
| 3. RNA/TP ($\mu g/mg$) | $26.632 \pm 0.652$ | $24.769 \pm 0.913$ incapacitation (−)1.863 (−)7.0% | $26.843 \pm 0.766$ recapacitation (+)2.074 (+)7.7% | |
| significance | $p < 0.001$ | $p < 0.001$ | 111.3% |
| 4. | $24.7 \pm 1.1\%$ | $34.4 \pm 1.3\%$ | $28.9 \pm 0.8\%$ | |

TABLE 5-continued

Results of the calculated indicators derived from the ratios between informational macromolecules, extracted from the brains (telencephalon and diencephalon) of normal rats (age: 8–9 months), incapacitated by global stress (wear and tear accumulated gradually over 17 months) and therapeutically revitalized with anti-stress, anti-impairment and anti-aging drug, in accordance with this invention.

| Brains (groups) Informational macromolecules | Normal (age: 8–9 months) ($\bar{x} \pm S.D.$) | Incapacitated by global stress ($\bar{x} \pm S.D.$) | Therapeutically revitalized (recapacited) ($\bar{x} \pm S.D.$) | Efficiency of revitalization |
|---|---|---|---|---|
| (WIP/TP) ×100 (%) significance | | incapacitation (+)9.70 (+)28.2% $p < 0.001$ | recapacitation (−)5.42 (−)15.8% $p < 0.001$ | 55.9% |

TP: total proteins;
WIP: water insoluble proteins;
WSP: water soluble proteins;
for indicators nos. 1 and 3 normal brains = 100%;
for indicator nos. 2 and 4 incapacitated brains = 100%.

TABLE 6

Results of the stages and mechanisms (I–IX) of brain therapeutic revitalization (cellular, subcellular and macromolecular) achieved by the anti-oxidative and anti-catabolic stress actions (1–6) of the drug, in accordance with this invention.

| Action | Stage and mechanism of therapeutic revitalization |
|---|---|
| 1. Anti-lipofuscinopoietic action | I anti-catabolic pluriorganelle protection (mitochondrial mainly), by inhibition of the lipofuscin pigment formation (wear and tear pigment, tertiary lysosomes, old lysosomes, nonfunctional insoluble peroxidated subcellular wastes). |
| 2. Neuronal lipofuscinolytic action | II breaking up of the aggregated pigment conglomerates, by successive disintegration. III vacuolation of the nonfunctional insoluble subcellular residues, by solubilization. |
| 3. Neurono-glial lipofuscin transfer | IV accumulation in the neurosomal peripherical zones of the subcellular wastes previously processed (broken up and vacuolated). by intracellular transport into the neuron. V elimination of the processed subcellular residues from the neuron, by neurono-glial intercellular transfer. VI collection of the transferred subcellular wastes into the perineuronal glias (particularly into microglias, then into astrocytes and oligodendrocytes) and their intraglial processing (vacuolation), by glial intracellular transport and by solubilization, respectively. |
| 4. Glial lipofuscinolytic action | VII removal of the vacuolated subcellular residues from the perineuronal glias, their gathering in the pericapillary glias and areas (in the vascular end-feet of astro- and microglias and in the pericytes) and continuation of the intraglial processing (vacuolation). by glial intracellular transport, by glio-glial intercellular transfer or by migration of the microglias towards the vascular pole of the neuropil, and by solubilization, respectively. |
| 5. Capillary lipofuscinolytic action | VIII elimination of the vacuolated subcellular wastes from pericapillary glias and areas, and their accumulation in the endothelial cells, by glio-endothelial intercellular transfer. |
| 6. Capillary lipofuscin elimination | IX processing of the transferred subcellular residues (vacuolation) and their removal from the endothelial cells. by solubilization and by their outflow into the capillary lumen, respectively. |

TABLE 7

Results of the stages and mechanisms (I–VIII) of brain therapeutic revitalization (cellular, subcellular and macromolecular) achieved by the actions (1–5) with anabolic anti-stress consequences of the drug, in accordance with this invention.

| Action | Stage and mechanism of therapeutic revitalization | |
|---|---|---|
| 1. Action of primary anabolic organelle regeneration in neurosome | I | dispersed anabolic monoorganelle repopulation with free ribosomes and rough endoplasmic reticulum, by regulation and activation of the nerve cell genetic apparatus. |
| | II | intensive anabolic monoorganelle repopulation, by the emergence of some subcellular areas of massive regeneration with free ribosomes and rough endoplasmic reticulum, accompanied by hyperfunctional diversification of the reticulum (parallel disposing, anastomosing, hyperactive dilatation). by enhancement of ribonucleic acid biosynthesis and protein biosynthesis. |
| 2. Action of secondary anabolic organelle regeneration in neurosome | III | intensive anabolic polyorganelle repopulation, concentrated upon three groups of subcellular organelles; anabolic (free ribosomes, rough endoplasmic reticulum, Golgi apparatus), energetic (mitochondria) and contractile (neurofilaments, microtubules), by stimulation of the functional and structural anabolism. |
| 3. Action of anabolic organelle protection in neurosome | IV | protection of anabolic organelles (increase of their functional and life periods), by achievement of the optimal repartition and ratios between the anabolic process organelles, and also between these and the catabolic, contractile and energetic organelles. |
| 4. Action of axonal normalization | V | revitalization of the axoplasm and of the afferent organelles, by normalization of axoplasmic flow and as a consequence of the neurosomal subcellular organelle regeneration (stages I–IV). |
| | VI | normalization of the myelin sheath. by regeneration of the oligodendrocyte anabolic subcellular components, which causes the normal and accelerated glial lipoprotein synthesis. |
| 5. Action of synaptic normalization | VII | normalization of the subcellular organelles from the synaptic knobs, through axoplasmic flow. |
| | VIII | regeneration of the dendritic spines, in close correlation with the normalization of the terminal buttons (stage VII) and with the revitalization of the neurosomal subcellular components (stages I–IV). |

What is claimed is:

1. An anti-stress, anti-impairment and anti-aging drug for prophylactic, therapeutic and restorative use, the drug being a synergistic biological, neurometabolic and cell-trophic composition, and a pro-drug/drug, consisting of:
   a) 20.1%–52.3% anti-oxidative and anti-catabolic stress components selected from the group consisting of methionine, aminoethanol phenoxyacetates and phenoxyacetamides;
   b) 7.0%–35.1% anti-anabolic stress compounds selected from the group consisting of hydrooxopyrimidine carboxylates, oxopyrrolidine acetamides with potassium, zinc and lithium salts;
   c) 6.7%–8.6% vasodilative and normolipidemic active components selected from the group consisting of nicotinic alcohol, nicotinic acid, derivatives of nicotinamide, and derivatives of magnesium nicotinate, with magnesium and iodine salts; and
   d) 16.6%–19.9% energo-active and anti-toxic active components, selected from the group consisting of aspartate, fructose, vitamin $B_1$, vitamin $B_6$, monoacid phosphate and sulfate as salts, substances with double function, belonging to both classes.

2. The anti-stress, anti-impairment and anti-aging drug, according to claim 1, wherein it comprises the following active components: a) 18.0%–19.1% methionine; b) aminoethanol phenoxyacetates selected from the group consisting of meclofenoxate, which is 31.0%–33.1%, meclosulfonate, eclofenoxate, adafenoxate in a weight ratio of 1/0.65–1/0.72, 1/0.79–1/0.83 and 1/0.20–1/0.26 respectively, compared to the amount of meclofenoxate; c) aminoethyl phenoxyacetamides selected from the group consisting of mefexamide, fenoxedil, fexicaine, fipexide in a weight ration of 1/0.24–1/0.29, 1/0.07–1/0.08, 1/0.10–1/0.13 and 1/0.24–1/0.29 respectively, compared to the amount of meclofenoxate; d) 18.8%–20.0% hydrooxopyrimidine carboxylates selected from the group consisting of orotic acid and orotates of bioelements of the drug; e) oxopyrrolidine acetamides selected from the group consisting of piracetam, which is 29.3%–31.4%, oxiracetam, etiracetam, dimethylphenyl piracetam, pramiracetam or aniracetam in a weight ratio of 1/0.39–1/0.44, 1/0.28–1/0.34, 1/0.15–1/0.16, 1/0.44–1/0.48 and 1/0.50–1/0.53 respectively, compared to the amount of piracetam; f) 2.5%–2.9% potassium; g) 0.3%–0.7% zinc; h) 0.025%–0.033% lithium; i) 5.2%–6.6% nicotine derivatives selected from the group consisting of nicotinic alcohol, nicotine acid, nicotinamide and magnesium nicotinate; j) 1.5%–1.9% magnesium; k) 0.005%–0.007% iodine; l) 9.7%–10.6% aspartate; m) 1.7%–2.0% fructose; n) 0.9%–1.3% vitamin $B_1$; o) 1.2%–1.5% vitamin $B_6$; p) 2.6%–3.5% monoacid phosphate; q) 0.5%–1.0% sulfate; the percentages being related to 100 g of minimum daily active dose.

3. The anti-stress, anti-impairment and anti-aging drug, according to claim 1, wherein its active components are contained in two pharmaceutical units, complementary regarding the bioavailability and the therapeutic action of the drug, wherein:
   a) the first unit comprises a gastrosoluble capsule or coated tablet comprising: 240 mg.–280 mg meclofenoxate hydrochloride, 135 mg–165 mg DL methionine, 80 mg–100 mg anhydrous DL magnesium asparate, 9 mg–11 mg D(-) fructose, 7 mg–9 mg vitamin $B_1$ hydrochloride, 10 mg–12 mg vitamin $B_6$ hydrochloride, 9 mg–11 mg non-retarded nicotinic acid with immediate-release and 9 mg–11 mg anhydrous zinc sulfate, and b) the second unit comprises an enterosoluble capsule or coated tablet comprising: 290 mg–340 mg anhydrous orotic acid, 9 mg–11 mg D(-) fructose, 70 mg–90 mg retarded nicotinic acid with prolonged-release, 88 mg–108 mg anhydrous dipotassium phosphate, 18 mg–22 mg magnesium oxide, 2 mg–3 mg lithium carbonate and 0.1 mg–0.14 mg potassium iodide.

4. The anti-stress, anti-impairment and anti-aging drug according to claim 3, wherein the gastrosoluble capsule is prepared by granulating the meclofenoxate or its related compounds, mixing in other components in powder form, and encasing the mixture in gelatin capsules, the enterosoluble capsule being prepared by granulating the nicotinic acid or its deriatives, mixing in other components in powder form, encasing the mixture in gelatin capsules, and enteric coating the capsules in aqueous dispersion or in organic solvent solution.

5. The anti-stress, anti-impairment and anti-aging drug according to claim 3, wherein the gastrosoluble capsule is prepared by compressing the meclofenoxate or its related compounds, mixing in other components in powder form, encasing the mixture in gelatin capsules, and coating the capsules with a film obtained from a gastrosoluble polymer in aqueous dispersion or in organic solvent solution, the enterosoluble capsule being prepared by granulating the nicotinic acid or its derivatives, compressing the nicotinic acid or its derivatives, mixing in other components in powder form, encasing the mixture in gelatin capsules, and enteric coating the capsules in aqueous dispersion or in organic solvent solution.

6. The anti-stress, anti-impairment and anti-aging drug according to claim 4, wherein the prolonged release of the vasodilative compound in the enterosoluble unit is selected from the group consisting of nicotinic alcohol, nicotinic acid, deriatives of nicotinamide, derivatives of magnesium nicotinate, is achieved depending on time necessary for releasing the active substance, in the form of a retarded granule, using ethyl cellulose as a first retardant and diethyl phthalate as a plasticizer in a weight ratio of 1/0.18–1/0.24, followed by granule coating with carnauba wax as the second retardant, in a weight ratio of 1/0.47–1/0.53 compared to ethyl cellulose, or in the form of a retarded tablet, obtained by compressing the retarded granule.

7. The anti-stress, anti-impairment and anti-aging drug according to claim 5, wherein the prolonged release of the vasodilative compound in the enterosoluble unit is selected from the group consisting of nicotinic alcohol, nicotinic acid, derivatives of nicotinamide, derivatives of magnesium nicotinate, is achieved depending on time necessary for releasing the active substance, in the form of a retarded tablet, obtained by compressing the retarded granulate, using ethyl cellulose as a first retardant and diethyl phthalate as a plasticizer in a weight ratio of 1/0.18–1/0.24, followed by granule coating with carnauba wax as the second retardant, in a weight ration of 1/0.47–1/0.53 compared to ethyl cellulose.

8. The anti-stress, anti-impairment and anti-aging drug according to claim 4, wherein the enteric coating is performed on gelatin capsules, filled with the enterosoluble unit composition, using the aqueous dispersion of a gastroresistant-enterosoluble polymer selected from the group consisting of cellulose acetate phthalate, polyvinyl acetate phthalate, hydroxypropyl methylcellulose phthalate or a methacrylic copolymer, in a mixture with a colorant and a plasticizer selected from the group consisting of diethyl phthalate, dibutylphthalate, propyleneglycol or triacetin, the weight ratio of enterosoluble polymer to plasticizer being within the range of 1/0.33–1/0.39 and the weight ratio of enterosoluble polymer to colorant being within the range of 1/0.0010–1/0.0012, as coating procedure using a fluidized bed, at an average temperature of 70° C., alternating the spraying and drying stages, and thus obtaining a final coating film of about 60 mg–70 mg/capsule.

9. The anti-stress, anti-impairment and anti-aging drug according to claim 5, wherein the enteric coating is performed on gelatin capsules, filled with the enterosoluble unit composition, using the aqueous dispersion of a gastroresistant-enterosoluble polymer selected from the group consisting of cellulose acetate phthalate, polyvinyl acetate phthalate, hydroxypropyl methylcellulose phthalate or a methacrylic copolymer, in a mixture with a colorant and a plasticizer selected from the group consisting of diethyl phthalate, dibutylphthalate, propyleneglycol or triacetin, the weight ratio of enterosoluble polymer to plasticizer being within the range of 1/0.33–1/0.39 and the weight ratio of enterosoluble polymer to colorant being within the range of 1/0.0010–1/0.0012, as coating procedure using a fluidized bed, at an average temperature of 70° C., alternating the spraying and drying stages, and thus obtaining a final coating film of about 60 mg–70 mg/capsule.

* * * * *